United States Patent
Levinson et al.

(10) Patent No.: US 11,219,549 B2
(45) Date of Patent: Jan. 11, 2022

(54) COOLING DEVICE HAVING A PLURALITY OF CONTROLLABLE COOLING ELEMENTS TO PROVIDE A PREDETERMINED COOLING PROFILE

(71) Applicant: Zeltiq Aesthetics, Inc., Pleasanton, CA (US)

(72) Inventors: Mitchell E. Levinson, Pleasanton, CA (US); Jesse N. Rosen, Albany, CA (US); William P. Pennybacker, Livermore, CA (US)

(73) Assignee: Zeltiq Aesthetics, Inc., Pleasanton, CA (US)

( * ) Notice: Subject to any disclaimer, the term of this patent is extended or adjusted under 35 U.S.C. 154(b) by 0 days.

(21) Appl. No.: 16/992,097

(22) Filed: Aug. 13, 2020

(65) Prior Publication Data

US 2020/0368061 A1 Nov. 26, 2020

Related U.S. Application Data

(63) Continuation of application No. 16/415,684, filed on May 17, 2019, which is a continuation of application
(Continued)

(51) Int. Cl.
*A61F 7/00* (2006.01)
*A61F 7/10* (2006.01)
(Continued)

(52) U.S. Cl.
CPC .............. *A61F 7/0085* (2013.01); *A61F 7/10* (2013.01); *A61B 18/14* (2013.01);
(Continued)

(58) Field of Classification Search
CPC ........ A61F 2007/029; A61F 2007/0075; A61F 2007/0076
See application file for complete search history.

(56) References Cited

U.S. PATENT DOCUMENTS

| 681,806 A | 9/1901 | Mignault |
| 889,810 A | 6/1908 | Robinson |

(Continued)

FOREIGN PATENT DOCUMENTS

| AU | 2011253768 A1 | 6/2012 |
| CA | 2441489 A1 | 3/2005 |

(Continued)

OTHER PUBLICATIONS

Aguilar et al., "Modeling Cryogenic Spray Temperature and Evaporation Rate Based on Single-Droplet Analysis," Eighth International Conference on Liquid Atomization and Spray Systems, Pasadena, CA, USA, Jul. 2000, 7 pages.

(Continued)

*Primary Examiner* — Kaitlyn E Smith
(74) *Attorney, Agent, or Firm* — Perkins Coie LLP

(57) ABSTRACT

A cooling device for removing heat from subcutaneous lipid-rich cells of a subject having skin is provided. The cooling device includes a plurality of cooling elements movable relative to each other to conform to the contour's of the subject's skin. The cooling elements have a plurality of controllable thermoelectric coolers. The cooling elements can be controlled to provide a time-varying cooling profile in a predetermined sequence, can be controlled to provide a spatial cooling profile in a selected pattern, or can be adjusted to maintain constant process parameters, or can be controlled to provide a combination thereof.

9 Claims, 12 Drawing Sheets

Related U.S. Application Data

No. 14/825,841, filed on Aug. 13, 2015, now Pat. No. 10,292,859, which is a continuation of application No. 13/616,186, filed on Sep. 14, 2012, now Pat. No. 9,375,345, which is a continuation of application No. 11/528,225, filed on Sep. 26, 2006, now Pat. No. 9,132,031.

(51) Int. Cl.
    *A61B 18/14*         (2006.01)
    *A61B 18/00*         (2006.01)
    *A61F 7/02*          (2006.01)

(52) U.S. Cl.
CPC ............... *A61B 2018/00011* (2013.01); *A61B 2018/00023* (2013.01); *A61B 2018/00047* (2013.01); *A61B 2018/00452* (2013.01); *A61B 2018/00476* (2013.01); *A61B 2018/00744* (2013.01); *A61B 2018/00791* (2013.01); *A61F 7/02* (2013.01); *A61F 2007/0001* (2013.01); *A61F 2007/0052* (2013.01); *A61F 2007/0054* (2013.01); *A61F 2007/0056* (2013.01); *A61F 2007/0075* (2013.01); *A61F 2007/0093* (2013.01); *A61F 2007/029* (2013.01)

(56) References Cited

U.S. PATENT DOCUMENTS

| | | |
|---|---|---|
| 1,093,868 A | 4/1914 | Leighty |
| 2,516,491 A | 7/1950 | Swastek |
| 2,521,780 A | 9/1950 | Dodd |
| 2,726,658 A | 12/1955 | Chessey |
| 2,766,619 A | 10/1956 | Myron et al. |
| 2,851,602 A | 9/1958 | Cramwinckel et al. |
| 3,093,135 A | 6/1963 | Hirschhorn |
| 3,132,688 A | 5/1964 | Nowak |
| 3,282,267 A | 11/1966 | William |
| 3,341,230 A | 9/1967 | Louis |
| 3,502,080 A | 3/1970 | Hirschhorn |
| 3,566,871 A | 3/1971 | Richter et al. |
| 3,587,577 A | 6/1971 | Smirnov et al. |
| 3,591,645 A | 7/1971 | Selwitz |
| 3,692,338 A | 9/1972 | Nick |
| 3,703,897 A | 11/1972 | Mack et al. |
| 3,710,784 A | 1/1973 | Taylor |
| 3,786,814 A | 1/1974 | Armao |
| 3,827,436 A | 8/1974 | Stumpf et al. |
| 3,942,519 A | 3/1976 | Shock |
| 3,948,269 A | 4/1976 | Zimmer |
| 3,986,385 A | 10/1976 | Johnston et al. |
| 3,993,053 A | 11/1976 | Grossan |
| 4,002,221 A | 1/1977 | Buchalter |
| 4,008,910 A | 2/1977 | Roche |
| 4,026,299 A | 5/1977 | Sauder |
| 4,140,130 A | 2/1979 | Storm |
| 4,149,529 A | 4/1979 | Copeland et al. |
| 4,178,429 A | 12/1979 | Scheffer |
| 4,202,336 A | 5/1980 | Van |
| 4,266,043 A | 5/1981 | Fujii et al. |
| 4,269,068 A | 5/1981 | Molina |
| 4,381,009 A | 4/1983 | Del |
| 4,396,011 A | 8/1983 | Mack et al. |
| 4,459,854 A | 7/1984 | Richardson et al. |
| 4,470,263 A | 9/1984 | Lehovec et al. |
| 4,483,341 A | 11/1984 | Witteles |
| 4,528,979 A | 7/1985 | Marchenko et al. |
| 4,531,524 A | 7/1985 | Mioduski |
| 4,548,212 A | 10/1985 | Leung |
| 4,555,313 A | 11/1985 | Duchane et al. |
| 4,585,002 A | 4/1986 | Kissin |
| 4,603,076 A | 7/1986 | Bowditch et al. |
| 4,614,191 A | 9/1986 | Perler |
| 4,644,955 A | 2/1987 | Mioduski |
| 4,664,110 A | 5/1987 | Schanzlin |
| 4,700,701 A | 10/1987 | Montaldi |
| 4,718,429 A | 1/1988 | Smidt |
| 4,741,338 A | 5/1988 | Miyamae |
| 4,758,217 A | 7/1988 | Gueret |
| 4,764,463 A | 8/1988 | Mason et al. |
| 4,802,475 A | 2/1989 | Weshahy |
| 4,832,022 A | 5/1989 | Tjulkov et al. |
| 4,846,176 A | 7/1989 | Golden |
| 4,850,340 A | 7/1989 | Onishi |
| 4,869,250 A | 9/1989 | Bitterly |
| 4,880,564 A | 11/1989 | Abel et al. |
| 4,905,697 A | 3/1990 | Heggs et al. |
| 4,906,463 A | 3/1990 | Cleary et al. |
| 4,930,317 A | 6/1990 | Klein |
| 4,935,345 A | 6/1990 | Guilbeau et al. |
| 4,961,422 A | 10/1990 | Marchosky et al. |
| 4,962,761 A | 10/1990 | Golden |
| 4,990,144 A | 2/1991 | Blott |
| 5,007,433 A | 4/1991 | Hermsdoerffer et al. |
| 5,018,521 A | 5/1991 | Campbell |
| 5,024,650 A | 6/1991 | Hagiwara et al. |
| 5,065,752 A | 11/1991 | Sessions et al. |
| 5,069,208 A | 12/1991 | Noppel et al. |
| 5,084,671 A | 1/1992 | Miyata et al. |
| 5,108,390 A | 4/1992 | Potocky et al. |
| 5,119,674 A | 6/1992 | Nielsen |
| 5,139,496 A | 8/1992 | Hed |
| 5,143,063 A | 9/1992 | Fellner |
| 5,148,804 A | 9/1992 | Hill et al. |
| 5,158,070 A | 10/1992 | Dory |
| 5,160,312 A | 11/1992 | Voelkel |
| 5,169,384 A | 12/1992 | Bosniak et al. |
| 5,197,466 A | 3/1993 | Marchosky et al. |
| 5,207,674 A | 5/1993 | Hamilton |
| 5,221,726 A | 6/1993 | Dabi et al. |
| 5,264,234 A | 11/1993 | Windhab et al. |
| 5,277,030 A | 1/1994 | Miller |
| 5,314,423 A | 5/1994 | Seney |
| 5,327,886 A | 7/1994 | Chiu |
| 5,330,745 A | 7/1994 | Mcdow |
| 5,333,460 A | 8/1994 | Lewis et al. |
| 5,334,131 A | 8/1994 | Omandam et al. |
| 5,336,616 A | 8/1994 | Livesey et al. |
| 5,339,541 A | 8/1994 | Owens |
| 5,342,617 A | 8/1994 | Gold |
| 5,351,677 A | 10/1994 | Kami et al. |
| 5,358,467 A | 10/1994 | Milstein et al. |
| 5,362,966 A | 11/1994 | Rosenthal et al. |
| 5,363,347 A | 11/1994 | Nguyen |
| 5,372,608 A | 12/1994 | Johnson |
| 5,386,837 A | 2/1995 | Sterzer |
| 5,411,541 A | 5/1995 | Bell et al. |
| 5,427,772 A | 6/1995 | Hagan |
| 5,433,717 A | 7/1995 | Rubinsky et al. |
| 5,456,703 A | 10/1995 | Beeuwkes |
| 5,472,416 A | 12/1995 | Blugerman et al. |
| 5,486,207 A | 1/1996 | Mahawili |
| 5,497,596 A | 3/1996 | Zatkulak |
| 5,501,655 A | 3/1996 | Rolt et al. |
| 5,505,726 A | 4/1996 | Meserol |
| 5,505,730 A | 4/1996 | Edwards |
| 5,507,790 A | 4/1996 | Weiss |
| 5,514,105 A | 5/1996 | Goodman et al. |
| 5,514,170 A | 5/1996 | Mauch |
| 5,531,742 A | 7/1996 | Barken |
| 5,558,376 A | 9/1996 | Woehl |
| 5,562,604 A | 10/1996 | Yablon et al. |
| 5,571,801 A | 11/1996 | Segall et al. |
| 5,575,812 A | 11/1996 | Owens |
| 5,603,221 A | 2/1997 | Maytal |
| 5,628,769 A | 5/1997 | Saringer |
| 5,634,890 A | 6/1997 | Morris |
| 5,634,940 A | 6/1997 | Panyard |
| 5,647,051 A | 7/1997 | Neer |
| 5,647,868 A | 7/1997 | Chinn |
| 5,650,450 A | 7/1997 | Lovette et al. |
| 5,651,773 A | 7/1997 | Perry et al. |
| 5,654,279 A | 8/1997 | Rubinsky et al. |

(56) References Cited

U.S. PATENT DOCUMENTS

| | | |
|---|---|---|
| 5,654,546 A | 8/1997 | Lindsay |
| 5,660,836 A | 8/1997 | Knowlton |
| 5,665,053 A | 9/1997 | Jacobs |
| 5,672,172 A | 9/1997 | Zupkas |
| 5,700,284 A | 12/1997 | Owens |
| 5,725,483 A | 3/1998 | Podolsky |
| 5,733,280 A | 3/1998 | Avitall |
| 5,741,248 A | 4/1998 | Stern et al. |
| 5,746,702 A | 5/1998 | Gelfgat et al. |
| 5,746,736 A | 5/1998 | Tankovich |
| 5,755,663 A | 5/1998 | Larsen et al. |
| 5,755,753 A | 5/1998 | Knowlton |
| 5,755,755 A | 5/1998 | Panyard |
| 5,759,182 A | 6/1998 | Varney et al. |
| 5,759,764 A | 6/1998 | Polovina |
| 5,769,879 A | 6/1998 | Richards et al. |
| 5,785,955 A | 7/1998 | Fischer |
| 5,792,080 A | 8/1998 | Ookawa et al. |
| 5,800,490 A | 9/1998 | Patz et al. |
| 5,802,865 A | 9/1998 | Strauss |
| 5,814,040 A | 9/1998 | Nelson et al. |
| 5,817,050 A | 10/1998 | Klein |
| 5,817,145 A | 10/1998 | Augustine |
| 5,817,149 A | 10/1998 | Owens |
| 5,817,150 A | 10/1998 | Owens |
| 5,830,208 A | 11/1998 | Muller |
| 5,833,685 A | 11/1998 | Tortal et al. |
| 5,844,013 A | 12/1998 | Kenndoff et al. |
| 5,853,364 A | 12/1998 | Baker et al. |
| 5,865,841 A | 2/1999 | Kolen et al. |
| 5,871,524 A | 2/1999 | Knowlton |
| 5,871,526 A | 2/1999 | Gibbs et al. |
| 5,885,211 A | 3/1999 | Eppstein et al. |
| 5,891,617 A | 4/1999 | Watson et al. |
| 5,895,418 A | 4/1999 | Saringer |
| 5,901,707 A | 5/1999 | Goncalves |
| 5,902,256 A | 5/1999 | Benaron |
| 5,919,219 A | 7/1999 | Knowlton |
| 5,944,748 A | 8/1999 | Mager et al. |
| 5,948,011 A | 9/1999 | Knowlton |
| 5,954,680 A | 9/1999 | Augustine |
| 5,964,092 A | 10/1999 | Tozuka et al. |
| 5,964,749 A | 10/1999 | Eckhouse et al. |
| 5,967,976 A | 10/1999 | Larsen et al. |
| 5,980,561 A | 11/1999 | Kolen et al. |
| 5,986,167 A | 11/1999 | Arteman et al. |
| 5,989,286 A | 11/1999 | Owens |
| 5,997,530 A | 12/1999 | Nelson et al. |
| 6,017,337 A * | 1/2000 | Pira ................... A61B 18/02 601/15 |
| 6,023,932 A | 2/2000 | Johnston |
| 6,032,675 A | 3/2000 | Rubinsky |
| 6,039,694 A | 3/2000 | Larson et al. |
| 6,041,787 A | 3/2000 | Rubinsky |
| 6,047,215 A | 4/2000 | Mcclure et al. |
| 6,049,927 A | 4/2000 | Thomas et al. |
| 6,051,159 A | 4/2000 | Hao |
| 6,071,239 A | 6/2000 | Cribbs et al. |
| 6,074,415 A | 6/2000 | Der |
| 6,093,230 A | 7/2000 | Johnson et al. |
| 6,102,885 A | 8/2000 | Bass |
| 6,104,952 A | 8/2000 | Tu et al. |
| 6,104,959 A | 8/2000 | Spertell |
| 6,106,517 A | 8/2000 | Zupkas |
| 6,113,558 A | 9/2000 | Rosenschein et al. |
| 6,113,559 A | 9/2000 | Klopotek |
| 6,113,626 A | 9/2000 | Clifton et al. |
| 6,120,519 A | 9/2000 | Weber et al. |
| 6,139,544 A | 10/2000 | Mikus et al. |
| 6,150,148 A | 11/2000 | Nanda et al. |
| 6,151,735 A | 11/2000 | Koby et al. |
| 6,152,952 A | 11/2000 | Owens |
| 6,171,301 B1 | 1/2001 | Nelson et al. |
| 6,180,867 B1 | 1/2001 | Hedengren et al. |
| 6,226,996 B1 | 5/2001 | Weber et al. |
| 6,241,753 B1 | 6/2001 | Knowlton |
| 6,264,649 B1 | 7/2001 | Whitcroft et al. |
| 6,273,884 B1 | 8/2001 | Altshuler et al. |
| 6,290,988 B1 | 9/2001 | Van et al. |
| 6,311,090 B1 | 10/2001 | Knowlton |
| 6,311,497 B1 | 11/2001 | Chung |
| 6,312,453 B1 | 11/2001 | Stefanile et al. |
| 6,350,276 B1 | 2/2002 | Knowlton |
| 6,354,297 B1 | 3/2002 | Eiseman |
| 6,357,907 B1 | 3/2002 | Cleveland et al. |
| 6,375,673 B1 | 4/2002 | Clifton et al. |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,401,722 B1 | 6/2002 | Krag |
| 6,405,090 B1 | 6/2002 | Knowlton |
| 6,413,255 B1 | 7/2002 | Stern |
| 6,425,912 B1 | 7/2002 | Knowlton |
| 6,426,445 B1 | 7/2002 | Young et al. |
| 6,430,446 B1 | 8/2002 | Knowlton |
| 6,430,956 B1 | 8/2002 | Haas et al. |
| 6,438,424 B1 | 8/2002 | Knowlton |
| 6,438,954 B1 | 8/2002 | Goetz et al. |
| 6,438,964 B1 | 8/2002 | Giblin |
| 6,453,202 B1 | 9/2002 | Knowlton |
| 6,458,888 B1 | 10/2002 | Hood et al. |
| 6,461,378 B1 | 10/2002 | Knowlton |
| 6,470,216 B1 | 10/2002 | Knowlton |
| 6,471,693 B1 | 10/2002 | Carroll et al. |
| 6,475,211 B2 | 11/2002 | Chess et al. |
| 6,478,811 B1 | 11/2002 | Dobak et al. |
| 6,494,844 B1 | 12/2002 | Van et al. |
| 6,497,721 B2 | 12/2002 | Ginsburg et al. |
| 6,508,831 B1 | 1/2003 | Kushnir |
| 6,514,244 B2 | 2/2003 | Pope et al. |
| 6,519,964 B2 | 2/2003 | Bieberich |
| 6,523,354 B1 | 2/2003 | Tolbert |
| 6,527,765 B2 | 3/2003 | Kelman et al. |
| 6,527,798 B2 | 3/2003 | Ginsburg et al. |
| 6,544,248 B1 | 4/2003 | Bass |
| 6,547,811 B1 | 4/2003 | Becker et al. |
| 6,548,297 B1 | 4/2003 | Kuri-harcuch et al. |
| 6,551,255 B2 | 4/2003 | Van et al. |
| 6,551,341 B2 | 4/2003 | Boylan et al. |
| 6,551,348 B1 | 4/2003 | Blalock et al. |
| 6,551,349 B2 | 4/2003 | Lasheras et al. |
| 6,569,189 B1 | 5/2003 | Augustine et al. |
| 6,585,652 B2 | 7/2003 | Lang et al. |
| 6,592,577 B2 | 7/2003 | Abboud et al. |
| 6,605,080 B1 | 8/2003 | Altshuler et al. |
| 6,607,498 B2 | 8/2003 | Eshel |
| 6,620,187 B2 | 9/2003 | Carson et al. |
| 6,620,188 B1 | 9/2003 | Ginsburg et al. |
| 6,620,189 B1 | 9/2003 | Machold et al. |
| 6,623,430 B1 | 9/2003 | Slayton et al. |
| 6,626,854 B2 | 9/2003 | Friedman et al. |
| 6,632,219 B1 | 10/2003 | Baranov et al. |
| 6,635,053 B1 | 10/2003 | Lalonde et al. |
| 6,643,535 B2 | 11/2003 | Damasco et al. |
| 6,645,162 B2 | 11/2003 | Friedman et al. |
| 6,645,229 B2 | 11/2003 | Matsumura et al. |
| 6,645,232 B2 | 11/2003 | Carson |
| 6,648,904 B2 | 11/2003 | Altshuler et al. |
| 6,656,208 B2 | 12/2003 | Grahn et al. |
| 6,660,027 B2 | 12/2003 | Gruszecki et al. |
| 6,662,054 B2 | 12/2003 | Kreindel et al. |
| 6,682,524 B1 | 1/2004 | Elbrecht et al. |
| 6,682,550 B2 | 1/2004 | Clifton et al. |
| 6,685,731 B2 | 2/2004 | Kushnir et al. |
| 6,694,170 B1 | 2/2004 | Mikus et al. |
| 6,695,874 B2 | 2/2004 | Machold et al. |
| 6,697,670 B2 | 2/2004 | Chomenky et al. |
| 6,699,237 B2 | 3/2004 | Weber et al. |
| 6,699,266 B2 | 3/2004 | Lachenbruch et al. |
| 6,699,267 B2 | 3/2004 | Voorhees et al. |
| 6,718,785 B2 | 4/2004 | Bieberich |
| 6,741,895 B1 | 5/2004 | Gafni et al. |

(56) References Cited

U.S. PATENT DOCUMENTS

| | | |
|---|---|---|
| 6,743,222 B2 | 6/2004 | Durkin et al. |
| 6,746,474 B2 | 6/2004 | Saadat |
| 6,749,624 B2 | 6/2004 | Knowlton |
| 6,753,182 B1 | 6/2004 | Kadkade et al. |
| 6,764,493 B1 | 7/2004 | Weber et al. |
| 6,764,502 B2 | 7/2004 | Bieberich |
| 6,789,545 B2 | 9/2004 | Littrup et al. |
| 6,795,728 B2 | 9/2004 | Chornenky et al. |
| 6,820,961 B2 | 11/2004 | Johnson |
| 6,821,274 B2 | 11/2004 | Mchale et al. |
| 6,840,955 B2 | 1/2005 | Ein |
| 6,849,075 B2 | 2/2005 | Bertolero et al. |
| 6,878,144 B2 | 4/2005 | Altshuler et al. |
| 6,889,090 B2 | 5/2005 | Kreindel |
| 6,892,099 B2 | 5/2005 | Jaafar et al. |
| 6,904,956 B2 | 6/2005 | Noel |
| 6,918,903 B2 | 7/2005 | Bass |
| 6,927,316 B1 | 8/2005 | Faries et al. |
| 6,942,022 B2 | 9/2005 | Blangetti et al. |
| 6,945,942 B2 | 9/2005 | Van et al. |
| 6,948,903 B2 | 9/2005 | Ablabutyan et al. |
| 6,969,399 B2 | 11/2005 | Schock et al. |
| 7,005,558 B1 | 2/2006 | Johansson et al. |
| 7,006,874 B2 | 2/2006 | Knowlton et al. |
| 7,022,121 B2 | 4/2006 | Stern et al. |
| 7,037,326 B2 | 5/2006 | Lee |
| 7,054,685 B2 | 5/2006 | Dimmer et al. |
| 7,060,061 B2 | 6/2006 | Altshuler et al. |
| 7,077,858 B2 | 7/2006 | Fletcher et al. |
| 7,081,111 B2 | 7/2006 | Svaasand et al. |
| 7,083,612 B2 | 8/2006 | Littrup et al. |
| 7,096,204 B1 | 8/2006 | Chen et al. |
| 7,112,712 B1 | 9/2006 | Ancell |
| 7,115,123 B2 | 10/2006 | Knowlton et al. |
| 7,141,049 B2 | 11/2006 | Stern et al. |
| 7,183,360 B2 | 2/2007 | Daniel et al. |
| 7,189,252 B2 | 3/2007 | Krueger |
| 7,192,426 B2 | 3/2007 | Baust et al. |
| 7,204,832 B2 | 4/2007 | Altshuler et al. |
| 7,220,778 B2 | 5/2007 | Anderson et al. |
| 7,229,436 B2 | 6/2007 | Stern et al. |
| 7,258,674 B2 | 8/2007 | Cribbs et al. |
| 7,267,675 B2 | 9/2007 | Stern et al. |
| 7,276,058 B2 | 10/2007 | Altshuler et al. |
| 7,318,821 B2 | 1/2008 | Lalonde et al. |
| 7,331,951 B2 | 2/2008 | Eshel et al. |
| 7,347,855 B2 | 3/2008 | Eshel et al. |
| 7,367,341 B2 | 5/2008 | Anderson et al. |
| 7,532,201 B2 | 5/2009 | Quistgaard et al. |
| 7,572,268 B2 | 8/2009 | Babaev |
| 7,604,632 B2 | 10/2009 | Howlett et al. |
| 7,613,523 B2 | 11/2009 | Eggers et al. |
| 7,615,016 B2 | 11/2009 | Barthe et al. |
| 7,713,266 B2 | 5/2010 | Elkins et al. |
| 7,780,656 B2 | 8/2010 | Tankovich |
| 7,799,018 B2 | 9/2010 | Goulko |
| 7,824,437 B1 | 11/2010 | Saunders |
| 7,828,831 B1 | 11/2010 | Tanhehco et al. |
| 7,850,683 B2 | 12/2010 | Elkins et al. |
| 7,854,754 B2 | 12/2010 | Ting et al. |
| 7,862,558 B2 | 1/2011 | Elkins et al. |
| RE42,277 E | 4/2011 | Jaafar et al. |
| 7,938,824 B2 | 5/2011 | Chornenky et al. |
| 7,959,657 B1 | 6/2011 | Harsy |
| 7,963,959 B2 | 6/2011 | Da et al. |
| 7,967,763 B2 | 6/2011 | Deem et al. |
| 7,993,330 B2 | 8/2011 | Goulko |
| 7,998,137 B2 | 8/2011 | Elkins et al. |
| RE42,835 E | 10/2011 | Chornenky et al. |
| RE43,009 E | 12/2011 | Chornenky et al. |
| 8,133,180 B2 | 3/2012 | Slayton et al. |
| 8,133,191 B2 | 3/2012 | Rosenberg et al. |
| 8,192,474 B2 | 6/2012 | Levinson |
| 8,246,611 B2 | 8/2012 | Paithankar et al. |
| 8,247,221 B2 | 8/2012 | Fawcett |
| 8,275,442 B2 | 9/2012 | Allison |
| 8,285,390 B2 | 10/2012 | Levinson et al. |
| 8,333,700 B1 | 12/2012 | Barthe et al. |
| 8,337,539 B2 | 12/2012 | Ting et al. |
| 8,366,622 B2 | 2/2013 | Slayton et al. |
| 8,372,130 B2 | 2/2013 | Young |
| 8,387,631 B1 | 3/2013 | Thonghara et al. |
| 8,397,518 B1 | 3/2013 | Vistakula |
| 8,414,631 B2 | 4/2013 | Quisenberry et al. |
| 8,433,400 B2 | 4/2013 | Prushinskaya et al. |
| 8,506,486 B2 | 8/2013 | Slayton et al. |
| 8,523,775 B2 | 9/2013 | Barthe et al. |
| 8,523,791 B2 | 9/2013 | Castel |
| 8,523,927 B2 | 9/2013 | Levinson et al. |
| 8,535,228 B2 | 9/2013 | O'connor et al. |
| 8,603,073 B2 | 12/2013 | Allison |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,676,332 B2 | 3/2014 | Fahey |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,702,774 B2 | 4/2014 | Baker et al. |
| 8,758,215 B2 | 6/2014 | Legendre et al. |
| 9,132,031 B2 | 9/2015 | Levinson et al. |
| 9,149,322 B2 | 10/2015 | Knowlton |
| 9,314,368 B2 | 4/2016 | Allison et al. |
| 9,375,345 B2 | 6/2016 | Levinson et al. |
| D777,338 S | 1/2017 | Coakley et al. |
| 9,581,942 B1 | 2/2017 | Shippert |
| 9,844,461 B2 | 12/2017 | Levinson et al. |
| 9,861,520 B2 | 1/2018 | Baker et al. |
| 10,292,859 B2 | 5/2019 | Levinson et al. |
| 10,383,787 B2 | 8/2019 | Rosen et al. |
| 10,568,759 B2 | 2/2020 | Yee et al. |
| 2001/0005791 A1 | 6/2001 | Ginsburg et al. |
| 2001/0023364 A1 | 9/2001 | Ahn |
| 2001/0031459 A1 | 10/2001 | Fahy et al. |
| 2001/0039439 A1 | 11/2001 | Elkins et al. |
| 2001/0045104 A1 | 11/2001 | Bailey et al. |
| 2001/0047196 A1 | 11/2001 | Ginsburg et al. |
| 2002/0026226 A1 | 2/2002 | Ein |
| 2002/0032473 A1 | 3/2002 | Kushnir et al. |
| 2002/0049483 A1 | 4/2002 | Knowlton |
| 2002/0058975 A1 | 5/2002 | Bieberich |
| 2002/0062142 A1 | 5/2002 | Knowlton |
| 2002/0068338 A1 | 6/2002 | Nanda et al. |
| 2002/0068874 A1 | 6/2002 | Zuckerwar et al. |
| 2002/0082668 A1 | 6/2002 | Ingman |
| 2002/0103520 A1 | 8/2002 | Latham |
| 2002/0107558 A1 | 8/2002 | Clifton et al. |
| 2002/0117293 A1 | 8/2002 | Campbell |
| 2002/0120315 A1 | 8/2002 | Furuno et al. |
| 2002/0128648 A1 | 9/2002 | Weber et al. |
| 2002/0151830 A1 | 10/2002 | Kahn |
| 2002/0151887 A1 | 10/2002 | Stern et al. |
| 2002/0156509 A1 | 10/2002 | Cheung |
| 2002/0188286 A1 | 12/2002 | Quijano et al. |
| 2002/0198518 A1 | 12/2002 | Mikus et al. |
| 2003/0032900 A1 | 2/2003 | Ella |
| 2003/0044764 A1 | 3/2003 | Soane et al. |
| 2003/0055414 A1 | 3/2003 | Altshuler et al. |
| 2003/0062040 A1 | 4/2003 | Lurie et al. |
| 2003/0069618 A1 | 4/2003 | Smith et al. |
| 2003/0077326 A1 | 4/2003 | Newton et al. |
| 2003/0077329 A1 | 4/2003 | Kipp et al. |
| 2003/0079488 A1 | 5/2003 | Bieberich |
| 2003/0100936 A1 | 5/2003 | Altshuler et al. |
| 2003/0109908 A1 | 6/2003 | Lachenbruch et al. |
| 2003/0109910 A1 | 6/2003 | Lachenbruch et al. |
| 2003/0109911 A1 | 6/2003 | Lachenbruch et al. |
| 2003/0109912 A1 | 6/2003 | Joye et al. |
| 2003/0114885 A1 | 6/2003 | Nova et al. |
| 2003/0120268 A1 | 6/2003 | Bertolero et al. |
| 2003/0125649 A1 | 7/2003 | Mcintosh et al. |
| 2003/0187488 A1 | 10/2003 | Kreindel et al. |
| 2003/0199226 A1 | 10/2003 | Sommer et al. |

(56) References Cited

U.S. PATENT DOCUMENTS

| | | |
|---|---|---|
| 2003/0199859 A1 | 10/2003 | Altshuler et al. |
| 2003/0220635 A1 | 11/2003 | Knowlton et al. |
| 2003/0220674 A1* | 11/2003 | Anderson ............. A61B 18/02 607/96 |
| 2003/0236487 A1 | 12/2003 | Knowlton |
| 2004/0002705 A1 | 1/2004 | Knowlton et al. |
| 2004/0006328 A1 | 1/2004 | Anderson |
| 2004/0009936 A1 | 1/2004 | Tang et al. |
| 2004/0024437 A1 | 2/2004 | Machold et al. |
| 2004/0030332 A1 | 2/2004 | Knowlton et al. |
| 2004/0034341 A1 | 2/2004 | Altshuler et al. |
| 2004/0039312 A1 | 2/2004 | Hillstead et al. |
| 2004/0044384 A1 | 3/2004 | Leber et al. |
| 2004/0049178 A1 | 3/2004 | Abboud et al. |
| 2004/0073079 A1 | 4/2004 | Altshuler et al. |
| 2004/0074629 A1 | 4/2004 | Noel |
| 2004/0077977 A1 | 4/2004 | Rave et al. |
| 2004/0082886 A1 | 4/2004 | Timpson |
| 2004/0093042 A1 | 5/2004 | Altshuler et al. |
| 2004/0104012 A1 | 6/2004 | Zhou et al. |
| 2004/0106867 A1 | 6/2004 | Eshel et al. |
| 2004/0116866 A1 | 6/2004 | Gorman et al. |
| 2004/0159109 A1 | 8/2004 | Harvie |
| 2004/0162596 A1 | 8/2004 | Altshuler et al. |
| 2004/0176667 A1 | 9/2004 | Mihai et al. |
| 2004/0186535 A1 | 9/2004 | Knowlton |
| 2004/0199226 A1 | 10/2004 | Shadduck |
| 2004/0206365 A1 | 10/2004 | Knowlton |
| 2004/0210214 A1 | 10/2004 | Knowlton |
| 2004/0210287 A1 | 10/2004 | Greene |
| 2004/0215294 A1 | 10/2004 | Littrup et al. |
| 2004/0249427 A1 | 12/2004 | Nabilsi |
| 2004/0259855 A1 | 12/2004 | Anderson et al. |
| 2004/0260209 A1 | 12/2004 | Ella et al. |
| 2004/0260210 A1 | 12/2004 | Ella et al. |
| 2004/0260211 A1 | 12/2004 | Maalouf |
| 2004/0267339 A1 | 12/2004 | Yon et al. |
| 2005/0010197 A1 | 1/2005 | Lau et al. |
| 2005/0033957 A1 | 2/2005 | Enokida |
| 2005/0049526 A1 | 3/2005 | Baer |
| 2005/0049661 A1 | 3/2005 | Koffroth |
| 2005/0113725 A1 | 5/2005 | Masuda |
| 2005/0143781 A1 | 6/2005 | Carbunaru et al. |
| 2005/0145372 A1 | 7/2005 | Noel |
| 2005/0149153 A1 | 7/2005 | Nakase et al. |
| 2005/0154314 A1 | 7/2005 | Quistgaard |
| 2005/0154431 A1 | 7/2005 | Quistgaard et al. |
| 2005/0159986 A1 | 7/2005 | Breeland et al. |
| 2005/0177075 A1 | 8/2005 | Meunier et al. |
| 2005/0182462 A1 | 8/2005 | Chornenky et al. |
| 2005/0187495 A1 | 8/2005 | Quistgaard et al. |
| 2005/0187597 A1 | 8/2005 | Vanderschuit |
| 2005/0203446 A1 | 9/2005 | Takashima |
| 2005/0215987 A1 | 9/2005 | Slatkine |
| 2005/0222565 A1 | 10/2005 | Manstein |
| 2005/0251117 A1 | 11/2005 | Anderson et al. |
| 2005/0251120 A1 | 11/2005 | Anderson et al. |
| 2005/0261753 A1 | 11/2005 | Littrup et al. |
| 2005/0283144 A1 | 12/2005 | Shiono et al. |
| 2006/0030778 A1 | 2/2006 | Mendlein et al. |
| 2006/0035380 A1 | 2/2006 | Saint-leger |
| 2006/0036300 A1 | 2/2006 | Kreindel |
| 2006/0041704 A1 | 2/2006 | Choi |
| 2006/0074313 A1 | 4/2006 | Slayton et al. |
| 2006/0079852 A1 | 4/2006 | Bubb et al. |
| 2006/0094988 A1 | 5/2006 | Tosaya et al. |
| 2006/0106836 A1 | 5/2006 | Masugi et al. |
| 2006/0111613 A1 | 5/2006 | Boutillette et al. |
| 2006/0122509 A1 | 6/2006 | Desilets |
| 2006/0188832 A1 | 8/2006 | McCarren |
| 2006/0189964 A1 | 8/2006 | Anderson et al. |
| 2006/0195168 A1 | 8/2006 | Dunbar et al. |
| 2006/0200063 A1 | 9/2006 | Munro et al. |
| 2006/0206040 A1 | 9/2006 | Greenberg |
| 2006/0206110 A1 | 9/2006 | Knowlton et al. |
| 2006/0234899 A1 | 10/2006 | Nekmard et al. |
| 2006/0259102 A1 | 11/2006 | Slatkine |
| 2006/0265032 A1 | 11/2006 | Hennings et al. |
| 2006/0270745 A1 | 11/2006 | Hunt et al. |
| 2006/0293734 A1 | 12/2006 | Scott et al. |
| 2007/0010811 A1 | 1/2007 | Stern et al. |
| 2007/0010861 A1 | 1/2007 | Anderson et al. |
| 2007/0032561 A1 | 2/2007 | Lin et al. |
| 2007/0038156 A1 | 2/2007 | Rosenberg |
| 2007/0055156 A1 | 3/2007 | Desilets et al. |
| 2007/0055173 A1 | 3/2007 | Delonzor et al. |
| 2007/0055179 A1 | 3/2007 | Deem et al. |
| 2007/0055180 A1 | 3/2007 | Deem et al. |
| 2007/0055181 A1 | 3/2007 | Deem et al. |
| 2007/0078502 A1 | 4/2007 | Weber et al. |
| 2007/0088413 A1 | 4/2007 | Weber et al. |
| 2007/0100398 A1 | 5/2007 | Sloan |
| 2007/0106342 A1 | 5/2007 | Schumann |
| 2007/0123962 A1 | 5/2007 | Grahn et al. |
| 2007/0129714 A1 | 6/2007 | Elkins et al. |
| 2007/0135876 A1 | 6/2007 | Weber |
| 2007/0141265 A1 | 6/2007 | Thomson |
| 2007/0179482 A1 | 8/2007 | Anderson |
| 2007/0198071 A1 | 8/2007 | Ting et al. |
| 2007/0219540 A1 | 9/2007 | Masotti et al. |
| 2007/0239075 A1 | 10/2007 | Rosenberg et al. |
| 2007/0239150 A1 | 10/2007 | Zvuloni et al. |
| 2007/0249519 A1 | 10/2007 | Guha et al. |
| 2007/0255187 A1 | 11/2007 | Branch |
| 2007/0255274 A1 | 11/2007 | Stern et al. |
| 2007/0255362 A1 | 11/2007 | Levinson et al. |
| 2007/0265585 A1 | 11/2007 | Joshi et al. |
| 2007/0265614 A1 | 11/2007 | Stern et al. |
| 2007/0270925 A1 | 11/2007 | Levinson |
| 2007/0282249 A1 | 12/2007 | Quisenberry et al. |
| 2007/0282318 A1 | 12/2007 | Spooner et al. |
| 2008/0014627 A1 | 1/2008 | Merchant et al. |
| 2008/0046047 A1 | 2/2008 | Jacobs |
| 2008/0058784 A1 | 3/2008 | Manstein et al. |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0097207 A1 | 4/2008 | Cai et al. |
| 2008/0139901 A1 | 6/2008 | Altshuler et al. |
| 2008/0140061 A1 | 6/2008 | Toubia et al. |
| 2008/0140371 A1 | 6/2008 | Warner |
| 2008/0160480 A1 | 7/2008 | Ruddle et al. |
| 2008/0161892 A1 | 7/2008 | Mercuro et al. |
| 2008/0183164 A1 | 7/2008 | Elkins et al. |
| 2008/0188915 A1 | 8/2008 | Mills et al. |
| 2008/0195036 A1 | 8/2008 | Merchant et al. |
| 2008/0248554 A1 | 10/2008 | Merchant et al. |
| 2008/0269851 A1 | 10/2008 | Deem et al. |
| 2008/0287839 A1 | 11/2008 | Rosen et al. |
| 2008/0300529 A1 | 12/2008 | Reinstein |
| 2008/0312651 A1 | 12/2008 | Pope et al. |
| 2009/0012434 A1 | 1/2009 | Anderson |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0024023 A1 | 1/2009 | Welches et al. |
| 2009/0054882 A1 | 2/2009 | Hansen et al. |
| 2009/0076488 A1 | 3/2009 | Welches et al. |
| 2009/0112134 A1 | 4/2009 | Avni |
| 2009/0118722 A1 | 5/2009 | Ebbers et al. |
| 2009/0149929 A1 | 6/2009 | Levinson et al. |
| 2009/0149930 A1 | 6/2009 | Schenck |
| 2009/0171253 A1 | 7/2009 | Davenport |
| 2009/0171334 A1 | 7/2009 | Elkins et al. |
| 2009/0209886 A1 | 8/2009 | Tudico |
| 2009/0221938 A1 | 9/2009 | Rosenberg et al. |
| 2009/0226424 A1 | 9/2009 | Hsu |
| 2009/0276018 A1 | 11/2009 | Brader |
| 2009/0281464 A1 | 11/2009 | Cioanta et al. |
| 2009/0299234 A1 | 12/2009 | Cho et al. |
| 2009/0306749 A1 | 12/2009 | Mulindwa |
| 2009/0312676 A1 | 12/2009 | Rousso et al. |

(56) References Cited

U.S. PATENT DOCUMENTS

| | | |
|---|---|---|
| 2009/0312693 A1 | 12/2009 | Thapliyal et al. |
| 2009/0318851 A1 | 12/2009 | Schenck |
| 2009/0326621 A1 | 12/2009 | El-Galley |
| 2010/0015190 A1 | 1/2010 | Hassler |
| 2010/0028969 A1 | 2/2010 | Mueller et al. |
| 2010/0030306 A1 | 2/2010 | Edelman et al. |
| 2010/0036295 A1 | 2/2010 | Altshuler et al. |
| 2010/0042087 A1 | 2/2010 | Goldboss et al. |
| 2010/0049178 A1 | 2/2010 | Deem et al. |
| 2010/0081971 A1 | 4/2010 | Allison |
| 2010/0087806 A1 | 4/2010 | Da et al. |
| 2010/0106230 A1 | 4/2010 | Buchanan et al. |
| 2010/0152824 A1 | 6/2010 | Allison |
| 2010/0168726 A1 | 7/2010 | Brookman |
| 2010/0179531 A1 | 7/2010 | Nebrigic et al. |
| 2010/0198064 A1 | 8/2010 | Perl et al. |
| 2010/0198204 A1 | 8/2010 | Rogers |
| 2010/0217349 A1 | 8/2010 | Fahey |
| 2010/0241023 A1 | 9/2010 | Gilbert |
| 2010/0268220 A1 | 10/2010 | Johnson et al. |
| 2010/0280582 A1 | 11/2010 | Baker et al. |
| 2011/0009860 A1 | 1/2011 | Chornenky et al. |
| 2011/0040235 A1 | 2/2011 | Castel |
| 2011/0040299 A1 | 2/2011 | Kim et al. |
| 2011/0046523 A1 | 2/2011 | Altshuler et al. |
| 2011/0060323 A1 | 3/2011 | Baust et al. |
| 2011/0066083 A1 | 3/2011 | Tosaya et al. |
| 2011/0066216 A1 | 3/2011 | Ting et al. |
| 2011/0077557 A1 | 3/2011 | Wing et al. |
| 2011/0077723 A1 | 3/2011 | Parish et al. |
| 2011/0112405 A1 | 5/2011 | Barthe et al. |
| 2011/0112520 A1 | 5/2011 | Michael |
| 2011/0144631 A1 | 6/2011 | Elkins et al. |
| 2011/0152849 A1 | 6/2011 | Baust et al. |
| 2011/0172651 A1 | 7/2011 | Altshuler et al. |
| 2011/0189129 A1 | 8/2011 | Qiu et al. |
| 2011/0196395 A1 | 8/2011 | Maschke |
| 2011/0196438 A1 | 8/2011 | Mnozil et al. |
| 2011/0202048 A1 | 8/2011 | Nebrigic |
| 2011/0238050 A1 | 9/2011 | Allison et al. |
| 2011/0238051 A1 | 9/2011 | Levinson et al. |
| 2011/0257642 A1 | 10/2011 | Griggs et al. |
| 2011/0288537 A1 | 11/2011 | Halaka |
| 2011/0300079 A1 | 12/2011 | Martens et al. |
| 2011/0301585 A1 | 12/2011 | Goulko |
| 2011/0313411 A1 | 12/2011 | Anderson et al. |
| 2011/0313412 A1 | 12/2011 | Kim et al. |
| 2012/0010609 A1 | 1/2012 | Deem et al. |
| 2012/0016239 A1 | 1/2012 | Barthe et al. |
| 2012/0022518 A1 | 1/2012 | Levinson |
| 2012/0022622 A1 | 1/2012 | Johnson et al. |
| 2012/0035475 A1 | 2/2012 | Barthe et al. |
| 2012/0035476 A1 | 2/2012 | Barthe et al. |
| 2012/0041525 A1 | 2/2012 | Kami |
| 2012/0046547 A1 | 2/2012 | Barthe et al. |
| 2012/0053458 A1 | 3/2012 | Barthe et al. |
| 2012/0065629 A1 | 3/2012 | Elkins et al. |
| 2012/0083862 A1 | 4/2012 | Altshuler et al. |
| 2012/0101549 A1 | 4/2012 | Schumann |
| 2012/0109041 A1 | 5/2012 | Munz |
| 2012/0158100 A1 | 6/2012 | Schomacker |
| 2012/0209363 A1 | 8/2012 | Williams et al. |
| 2012/0238901 A1 | 9/2012 | Augustine |
| 2012/0239123 A1 | 9/2012 | Weber et al. |
| 2012/0253416 A1 | 10/2012 | Erez et al. |
| 2012/0259322 A1 | 10/2012 | Fourkas et al. |
| 2012/0277674 A1 | 11/2012 | Clark et al. |
| 2012/0310232 A1 | 12/2012 | Erez |
| 2013/0018236 A1 | 1/2013 | Altshuler et al. |
| 2013/0019374 A1 | 1/2013 | Schwartz |
| 2013/0035680 A1 | 2/2013 | Ben-haim et al. |
| 2013/0066309 A1 | 3/2013 | Levinson |
| 2013/0073017 A1 | 3/2013 | Liu et al. |
| 2013/0079684 A1 | 3/2013 | Rosen et al. |
| 2013/0116758 A1 | 5/2013 | Levinson et al. |
| 2013/0116759 A1 | 5/2013 | Levinson et al. |
| 2013/0150844 A1 | 6/2013 | Deem et al. |
| 2013/0158440 A1 | 6/2013 | Allison |
| 2013/0158636 A1 | 6/2013 | Ting et al. |
| 2013/0166003 A1 | 6/2013 | Johnson et al. |
| 2013/0190744 A1 | 7/2013 | Avram et al. |
| 2013/0238062 A1 | 9/2013 | Ron Edoute et al. |
| 2013/0245507 A1 | 9/2013 | Khorassani Zadeh |
| 2013/0253384 A1 | 9/2013 | Anderson et al. |
| 2013/0303904 A1 | 11/2013 | Barthe et al. |
| 2013/0303905 A1 | 11/2013 | Barthe et al. |
| 2013/0331914 A1 | 12/2013 | Lee et al. |
| 2014/0005759 A1 | 1/2014 | Fahey et al. |
| 2014/0005760 A1 | 1/2014 | Levinson et al. |
| 2014/0142469 A1 | 5/2014 | Britva et al. |
| 2014/0163582 A1 | 6/2014 | Austen et al. |
| 2014/0200488 A1 | 7/2014 | Seo et al. |
| 2014/0228718 A1 | 8/2014 | Diller et al. |
| 2014/0277219 A1 | 9/2014 | Nanda |
| 2015/0209174 A1 | 7/2015 | Abreu |
| 2015/0216719 A1 | 8/2015 | Debenedictis et al. |
| 2015/0216720 A1 | 8/2015 | Debenedictis et al. |
| 2015/0216816 A1 | 8/2015 | O'Neil et al. |
| 2015/0283022 A1 | 10/2015 | Lee et al. |
| 2015/0328077 A1 | 11/2015 | Levinson |
| 2015/0335468 A1 | 11/2015 | Rose et al. |
| 2015/0342780 A1 | 12/2015 | Levinson et al. |
| 2016/0051308 A1 | 2/2016 | Pennybacker et al. |
| 2016/0051401 A1 | 2/2016 | Yee et al. |
| 2016/0324684 A1 | 11/2016 | Levinson et al. |
| 2017/0007309 A1 | 1/2017 | DeBenedictis et al. |
| 2017/0079833 A1 | 3/2017 | Frangineas, Jr. et al. |
| 2017/0105869 A1 | 4/2017 | Frangineas, Jr. et al. |
| 2017/0165105 A1 | 6/2017 | Anderson et al. |
| 2017/0196731 A1 | 7/2017 | DeBenedictis et al. |
| 2017/0239079 A1 | 8/2017 | Root et al. |
| 2017/0325992 A1 | 11/2017 | DeBenedictis et al. |
| 2017/0325993 A1 | 11/2017 | Jimenez Lozano et al. |
| 2017/0326042 A1 | 11/2017 | Zeng et al. |
| 2017/0326346 A1 | 11/2017 | Jimenez Lozano et al. |
| 2018/0161197 A1 | 6/2018 | Baker et al. |
| 2018/0185081 A1 | 7/2018 | O'neil et al. |
| 2018/0185189 A1 | 7/2018 | Weber et al. |
| 2018/0263677 A1 | 9/2018 | Hilton et al. |
| 2018/0271767 A1 | 9/2018 | Jimenez Lozano et al. |
| 2018/0310950 A1 | 11/2018 | Yee et al. |
| 2019/0125424 A1 | 5/2019 | DeBenedictis et al. |
| 2019/0142493 A1 | 5/2019 | DeBenedictis et al. |
| 2019/0365595 A1 | 12/2019 | Rosen et al. |

FOREIGN PATENT DOCUMENTS

| | | |
|---|---|---|
| CA | 2585214 A1 | 10/2007 |
| CH | 333982 A | 11/1958 |
| CN | 86200604 U | 10/1987 |
| CN | 2514795 Y | 10/2002 |
| CN | 2514811 Y | 10/2002 |
| CN | 1511503 A | 7/2004 |
| CN | 1741777 A | 3/2006 |
| CN | 1817990 A | 8/2006 |
| CN | 2843367 Y | 12/2006 |
| CN | 2850584 Y | 12/2006 |
| CN | 2850585 Y | 12/2006 |
| CN | 200970265 Y | 11/2007 |
| CN | 101259329 A | 9/2008 |
| CN | 101309657 A | 11/2008 |
| DE | 2851602 A1 | 6/1980 |
| DE | 4213584 A1 | 11/1992 |
| DE | 4224595 A1 | 1/1994 |
| DE | 4238291 A1 | 5/1994 |
| DE | 4445627 A1 | 6/1996 |
| DE | 19800416 A1 | 7/1999 |
| EP | 263069 A2 | 4/1988 |
| EP | 0397043 A1 | 11/1990 |
| EP | 0406244 A1 | 1/1991 |
| EP | 560309 A2 | 9/1993 |
| EP | 0598824 A1 | 6/1994 |
| EP | 1030611 A1 | 8/2000 |
| EP | 1201266 A1 | 5/2002 |

(56) References Cited

FOREIGN PATENT DOCUMENTS

| | | |
|---|---|---|
| EP | 1568395 A1 | 8/2005 |
| EP | 2289598 A1 | 3/2011 |
| EP | 2527005 A1 | 11/2012 |
| FR | 854937 A | 4/1940 |
| FR | 2744358 A1 | 8/1997 |
| FR | 2745935 A1 | 9/1997 |
| FR | 2767476 A1 | 2/1999 |
| FR | 2776920 A1 | 10/1999 |
| FR | 2789893 A1 | 8/2000 |
| FR | 2805989 A1 | 9/2001 |
| GB | 387960 A | 2/1933 |
| GB | 2120944 A | 12/1983 |
| GB | 2202447 A | 9/1988 |
| GB | 2248183 A | 4/1992 |
| GB | 2263872 A | 8/1993 |
| GB | 2286660 A | 8/1995 |
| GB | 2323659 A | 9/1998 |
| JP | 58187454 A | 11/1983 |
| JP | S6094113 A | 5/1985 |
| JP | 62082977 A | 4/1987 |
| JP | 63076895 A | 4/1988 |
| JP | 01223961 A | 9/1989 |
| JP | 03051964 A | 3/1991 |
| JP | 03259975 A | 11/1991 |
| JP | 04093597 A | 3/1992 |
| JP | 06261933 A | 9/1994 |
| JP | 07194666 A | 8/1995 |
| JP | 07268274 A | 10/1995 |
| JP | 09164163 A | 6/1997 |
| JP | 10216169 A | 8/1998 |
| JP | 10223961 A | 8/1998 |
| JP | 3065657 U | 4/1999 |
| JP | 2000503154 A | 3/2000 |
| JP | 2001046416 A | 2/2001 |
| JP | 2002125993 A | 5/2002 |
| JP | 2002224051 A | 8/2002 |
| JP | 2002282295 A | 10/2002 |
| JP | 2002290397 A | 10/2002 |
| JP | 2002543668 A | 12/2002 |
| JP | 2003190201 A | 7/2003 |
| JP | 2004013600 A | 1/2004 |
| JP | 2004073812 A | 3/2004 |
| JP | 2004159666 A | 6/2004 |
| JP | 2005039790 A | 2/2005 |
| JP | 3655820 B2 | 3/2005 |
| JP | 2005065984 A | 3/2005 |
| JP | 2005110755 A | 4/2005 |
| JP | 2005509977 A | 4/2005 |
| JP | 2005520608 A | 7/2005 |
| JP | 2005237908 A | 9/2005 |
| JP | 2005323716 A | 11/2005 |
| JP | 2006026001 A | 2/2006 |
| JP | 2006130055 A | 5/2006 |
| JP | 2006520949 A | 9/2006 |
| JP | 2007270459 A | 10/2007 |
| JP | 2008532591 A | 8/2008 |
| JP | 2009515232 A | 4/2009 |
| JP | 2009189757 A | 8/2009 |
| KR | 200173222 Y1 | 3/2000 |
| KR | 20040094508 A | 11/2004 |
| KR | 20090000258 U | 1/2009 |
| KR | 20130043299 A | 4/2013 |
| KR | 20140038165 A | 3/2014 |
| RU | 2036667 C1 | 6/1995 |
| SU | 532976 A1 | 11/1978 |
| TW | 0476644 B | 2/2002 |
| WO | 8503216 A1 | 8/1985 |
| WO | 9114417 A1 | 10/1991 |
| WO | 9300807 A1 | 1/1993 |
| WO | 9404116 A1 | 3/1994 |
| WO | 9623447 A1 | 8/1996 |
| WO | 9626693 A1 | 9/1996 |
| WO | 9636293 A1 | 11/1996 |
| WO | 9637158 A1 | 11/1996 |
| WO | 9704832 A1 | 2/1997 |
| WO | 9705828 A1 | 2/1997 |
| WO | 9722262 A2 | 6/1997 |
| WO | 9724088 A1 | 7/1997 |
| WO | 9725798 A1 | 7/1997 |
| WO | 9748440 A1 | 12/1997 |
| WO | 9829134 A2 | 7/1998 |
| WO | 9831321 A1 | 7/1998 |
| WO | 9841156 A1 | 9/1998 |
| WO | 9841157 A1 | 9/1998 |
| WO | 9909928 A1 | 3/1999 |
| WO | 9916502 A1 | 4/1999 |
| WO | 9938469 A1 | 8/1999 |
| WO | 9949937 A1 | 10/1999 |
| WO | 0044346 A1 | 8/2000 |
| WO | 0044349 A1 | 8/2000 |
| WO | 0065770 A1 | 11/2000 |
| WO | 0067685 A1 | 11/2000 |
| WO | 0100269 A1 | 1/2001 |
| WO | 0113989 A1 | 3/2001 |
| WO | 0114012 A1 | 3/2001 |
| WO | 0134048 A1 | 5/2001 |
| WO | 0205736 A1 | 1/2002 |
| WO | 02102921 A1 | 12/2002 |
| WO | 03007859 A1 | 1/2003 |
| WO | 03078596 A2 | 9/2003 |
| WO | 03079916 A1 | 10/2003 |
| WO | 2004000098 A2 | 12/2003 |
| WO | 2004080279 A2 | 9/2004 |
| WO | 2004090939 A2 | 10/2004 |
| WO | 2005033957 A1 | 4/2005 |
| WO | 2005046540 A1 | 5/2005 |
| WO | 2005060354 A2 | 7/2005 |
| WO | 2005096979 A1 | 10/2005 |
| WO | 2005112815 A1 | 12/2005 |
| WO | 2006066226 A1 | 6/2006 |
| WO | 2006094348 A1 | 9/2006 |
| WO | 2006106836 A1 | 10/2006 |
| WO | 2006116603 A2 | 11/2006 |
| WO | 2006127467 A2 | 11/2006 |
| WO | 2007012083 A2 | 1/2007 |
| WO | 2007028975 A1 | 3/2007 |
| WO | 2007041642 A2 | 4/2007 |
| WO | 2007101039 A1 | 9/2007 |
| WO | 2007127924 A2 | 11/2007 |
| WO | 2007145421 A1 | 12/2007 |
| WO | 2007145422 A1 | 12/2007 |
| WO | 2008006018 A2 | 1/2008 |
| WO | 2008039556 A1 | 4/2008 |
| WO | 2008039557 A1 | 4/2008 |
| WO | 2008055243 A2 | 5/2008 |
| WO | 2008143678 A1 | 11/2008 |
| WO | 2009011708 A1 | 1/2009 |
| WO | 2009026471 A1 | 2/2009 |
| WO | 2010077841 A1 | 7/2010 |
| WO | 2010127315 A2 | 11/2010 |
| WO | 2012012296 A1 | 1/2012 |
| WO | 2012103242 A1 | 8/2012 |
| WO | 2013013059 A1 | 1/2013 |
| WO | 2013075006 A1 | 5/2013 |
| WO | 2013075016 A1 | 5/2013 |
| WO | 2013190337 A1 | 12/2013 |
| WO | 2014151872 A3 | 12/2014 |
| WO | 2015117001 A1 | 8/2015 |
| WO | 2015117005 A1 | 8/2015 |
| WO | 2015117026 A2 | 8/2015 |
| WO | 2015117032 A1 | 8/2015 |
| WO | 2015117036 A2 | 8/2015 |
| WO | 2016028796 A1 | 2/2016 |
| WO | 2016048721 A1 | 3/2016 |

OTHER PUBLICATIONS

Al-Sakere, B. et al. "Tumor Ablation with Irreversible Electroporation," PLoS One, Issue 11, Nov. 2007, 8 pages.

Alster, T. et al., "Cellulite Treatment Using a Novel Combination Radiofrequency, Infrared Light, and Mechanical Tissue Manipulation Device," Journal of Cosmetic and Laser Therapy, vol. 7, 2005, pp. 81-85.

(56) References Cited

OTHER PUBLICATIONS

Ardevol, A. et al., "Cooling Rates of Tissue Samples During Freezing with Liquid Nitrogen," Journal of Biochemical and Biophysical Methods, vol. 27, 1993, pp. 77-86.
Arena, C. B. et al., "High-Frequency Irreversible Electroporation (H-FIRE) for Non-Thermal Ablation Without Muscle Contraction," BioMedical Engineering OnLine 2011, 10:102, Nov. 21, 2011, 21 pgs.
Becker, S. M. et al. "Local Temperature Rises Influence In Vivo Electroporation Pore Development: A Numerical Stratum Corneum Lipid Phase Transition Model," Journal of Biomechanical Engineering, vol. 129, Oct. 2007, pp. 712-721.
Bohm, T. et al., "Saline-Enhanced Radiofrequency Ablation of Breast Tissue: an in Vitro Feasibility Study," Investigative Radiology, vol. 35 (3), 2000, pp. 149-157.
Bondei, E. et al., "Disorders of Subcutaneous Tissue (Cold Panniculitis)," Dermatology in General Medicine, Fourth Edition, vol. 1, Chapter 108, 1993, Section 16, pp. 1333-1334.
Burge, S.M. et al., "Hair Follicle Destruction and Regeneration in Guinea Pig Skin after Cutaneous Freeze Injury," Cryobiology, 27(2), 1990, pp. 153-163.
Coban, Y. K. et al., "Ischemia-Reperfusion Injury of Adipofascial Tissue: An Experimental Study Evaluating Early Histologic and Biochemical Alterations in Rats," Mediators of Inflammation, 2005, 5, pp. 304-308.
Del Pino, M. E. et al. "Effect of Controlled Volumetric Tissue Heating with Radiofrequency on Cellulite and the Subcutaneous Tissue of the Buttocks and Thighs," Journal of Drugs in Dermatology, vol. 5, Issue 8, Sep. 2006, pp. 714-722.
Donski, P. K. et al., "The Effects of Cooling no Experimental Free Flap Survival," British Journal of Plastic Surgery, vol. 33, 1980, pp. 353-360.
Duck, F. A., Physical Properties of Tissue, Academic Press Ltd., chapters 4 & 5, 1990, pp. 73-165.
Duncan, W. C. et al., "Cold Panniculitis," Archives of Dermatology, vol. 94, Issue 6, Dec. 1966, pp. 722-724.
Epstein, E. H. et al., "Popsicle Panniculitis," The New England Journal of Medicine, 282(17), Apr. 23, 1970, pp. 966-967.
Fournier, L. et al. "Lattice Model for the Kinetics of Rupture of Fluid Bilayer Membranes," Physical Review, vol. 67, 2003, p. 051908-1-051908-11.
Gabriel, S. et al., "The Dielectric Properties Of Biological Tissues: II. Measurements in the Frequency Range 10 Hz to 20 GHz," Physics in Medicine and Biology, vol. 41, 1996, pp. 2251-2269.
Gage, A. "Current Progress in Cryosurgery," Cryobiology 25, 1988, pp. 483-486.
Gatto, H. "Effects of Thermal Shocks on Interleukin-1 Levels and Heat Shock Protein 72 (HSP72) Expression in Normal Human Keratinocytes," PubMed, Archives of Dermatological Research, vol. 284, Issue 7, 1992: pp. 414-417 [Abstract].
Hale, H. B. et al., "Influence of Chronic Heat Exposure and Prolonged Food Deprivation on Excretion of Magnesium, Phosphorus, Calcium, Hydrogen Ion & Ketones," Aerospace Medicine, vol. 39—No. 9, Sep. 1968, pp. 919-926.
Heller Page, E. et al., "Temperature-dependent skin disorders," Journal of the American Academy of Dermatology, vol. 18, No. 5, Pt 1, May 1988, pp. 1003-1019.
Hemmingsson, A. et al. "Attenuation in Human Muscle and Fat Tissue in Vivo and in Vitro," Aera Radiologica Diagnosis, vol. 23, No. 2, 1982, pp. 149-151.
Henry, F. et al., "Les Dermatoses Hivernales," Rev Med Liege, 54:11, 1999, pp. 864-866. [Abstract Attached].
Hernan, P. et al., "Study for the evaluation of the efficacy of Lipocryolysis (EEEL)", Nov. 30, 2011.
Hernan, R. P., "A Study to Evaluate the Action of Lipocryolysis", 33(3) CryoLellers, 2012, pp. 176-180.
Holland, DB. et al. "Cold shock induces the synthesis of stress proteins in human keratinocytes," PubMed Journal of Investigative Dermatology; 101(2): Aug. 1993, pp. 196-199.
Holman, W. L. et al., "Variation in Cryolesion Penetration Due to Probe Size and Tissue Thermal Conductivity," The Annals of Thoracic Surgery, vol. 53, 1992, pp. 123-126.
Hong, J.S. et al., "Patterns of Ice Formation in Normal and Malignant Breast Tissue," Cryobiology 31, 1994, pp. 109-120.
Huang et al. "Comparative Proteomic Profiling of Murine Skin," Journal of Investigative Dermatology, vol. 121(1), Jul. 2003, pp. 51-64.
Isambert, H. "Understanding the Electroporation of Cells and Artificial Bilayer Membranes," Physical Review Letters, vol. 80, No. 15, 1998, pp. 3404-3707.
Jalian, H. R. et al., "Cryolipolysis: A Historical Perspective and Current Clinical Practice", 32(1) Semin. Cutan. Med. Surg., 2013, pp. 31-34.
Kellum, R. E. et al., "Sclerema Neonatorum: Report of Case and Analysis of Subcutaneous and Epidermal-Dermal Lipids by Chromatographic Methods," Archives of Dermatology, vol. 97, Apr. 1968, pp. 372-380.
Koska, J. et al., "Endocrine Regulation of Subcutaneous Fat Metabolism During Cold Exposure in Humans," Annals of the New York Academy of Sciences, vol. 967, 2002, pp. 500-505.
Kundu, S. K. et al., "Breath Acetone Analyzer: Diagnostic Tool to Monitor Dietary Fat Loss," Clinical Chemistry, vol. 39, Issue (1), 1993, pp. 87-92.
Kundu, S. K. et al., "Novel Solid-Phase Assay of Ketone Bodies in Urine," Clinical Chemistry, vol. 37, Issue (9), 1991, pp. 1565-1569.
Kuroda, S. et al. "Thermal Distribution of Radio-Frequency Inductive Hyperthermia Using an Inductive Aperture-Type Applicator: Evaluation of the Effect of Tumor Size and Depth", Medical and Biological Engineering and Computing, vol. 37, 1999, pp. 285-290.
Laugier, P. et al., "In Vivo Results with a New Device for Ultrasonic Monitoring of Pig Skin Cryosurgery: The Echographic Cryprobe," The Society for Investigative Dermatology, Inc., vol. 111, No. 2, Aug. 1998, pp. 314-319.
Levchenko et al., "Effect of Dehydration on Lipid Metabolism" Ukrainskii Biokhimicheskii Zhurnal, vol. 50, Issue 1, 1978, pp. 95-97.
Lidagoster, MD et al., "Comparison of Autologous Fat Transfer in Fresh, Refrigerated, and Frozen Specimens: An Animal Model," Annals of Plastic Surgery, vol. 44, No. 5, May 2000, pp. 512-515.
Liu, A. Y.-C et al., "Transient Cold Shock Induces the Heat Shock Response upon Recovery at 37° C. in Human Cells," Journal of Biological Chemistry, , 269(20), May 20, 1994, p. 14768-14775.
L'Vova, S.P. "Lipid Levels and Lipid Peroxidation in Frog Tissues During Hypothermia and Hibernation" Ukrainskii Biokhimicheskii Zhurnal, vol. 62, Issue 1, 1990, pp. 65-70.
Maize, J.C. "Panniculitis," Cutaneous Pathology, Chapter 13, 1998, 327-344.
Malcolm, G. T. et al., "Fatty Acid Composition of Adipose Tissue in Humans: Differences between Subcutaneous Sites," The American Journal of Clinical Nutrition, vol. 50, 1989, pp. 288-291.
Manstein, D. et al. "A Novel Cryotherapy Method of Non-invasive, Selective Lipolysis," LasersSurg.Med 40:S20, 2008, p. 104.
Manstein, D. et al. "Selective Cryolysis: A Novel Method of Non-Invasive Fat Removal," Lasers in Surgery and Medicine: The Official Journal of the ASLMS, vol. 40, No. 9, Nov. 2008, pp. 595-604.
Mayoral, "Case Reports: Skin Tightening with a Combined Unipolar and Bipolar Radiofrequency Device," Journal of Drugs in Dermatology, 2007, pp. 212-215.
Mazur, P. "Cryobiology: The Freezing of Biological Systems," Science, 68, 1970, pp. 939-949.
Merrill, T. "A Chill to the Heart: A System to Deliver Local Hypothermia Could One Day Improve the Lives of Heart-Attack Patients," Mechanical Engineering Magazine, Oct. 2010, 10 pages.
Miklavcic, D. et al. "Electroporation-Based Technologies and Treatments," The Journal of Membrane Biology (2010) 236:1-2, 2 pgs.
Moschella, S. L. et al., "Diseases of the Subcutaneous Tissue," in Dermatology, Second Edition, vol. 2, 1985 Chapter 19, Section II (W.B. Saunders Company, 1980) pp. 1169-1181.
Murphy, J. V. et al., "Frostbite: Pathogenesis and Treatment" The Journal of Trauma: Injury, Infection, and Critical Care, vol. 48, No. 1, Jan. 2000, pp. 171-178.

(56) References Cited

OTHER PUBLICATIONS

Nagao, T. et al., "Dietary Diacylglycerol Suppresses Accumulation of Body Fat Compared to Triacylglycerol in Men a Double-Blind Controlled Trial," The Journal of Nutrition, vol. 130, Issue (4), 2000, pp. 792-797.
Nagle, W. A. et al. "Cultured Chinese Hamster Cells Undergo Apoptosis After Exposure to Cold but Nonfreezing Temperatures," Cryobiology 27, 1990, pp. 439-451.
Nagore, E. et al., "Lipoatrophia Semicircularis-a Traumatic Panniculitis: Report of Seven Cases and Review of the Literature," Journal of the American Academy of Dermatology, vol. 39, Nov. 1998, pp. 879-881.
Nanda, G.S. et al., "Studies on electroporation of thermally and chemically treated human erythrocytes," Bioelectrochemistry and Bioenergetics, 34, 1994, pp. 129-134, 6 pgs.
Narins, D.J. et al. "Non-Surgical Radiofrequency Facelift", The Journal of Drugs in Dermatology, vol. 2, Issue 5, 2003, pp. 495-500.
Nielsen, B. "Thermoregulation in Rest and Exercise," Acta Physiologica Scandinavica Suppiementum, vol. 323 (Copenhagen 1969), pp. 7-74.
Nishikawa, H. et al. "Ultrastructural Changes and Lipid Peroxidation in Rat Adipomusculocutaneous Flap Isotransplants after Normothermic Storage and Reperfusion," Transplantation, vol. 54, No. 5, 1992, pp. 795-801.
Nurnberger, F. "So-Called Cellulite: An Invented Disease," Journal of Dermatologic Surgery and Oncology, Mar. 1978, pp. 221-229.
Pease, G. R. et al., "An Integrated Probe for Magnetic Resonance Imaging Monitored Skin Cryosurgery," Journal of Biomedical Engineering, vol. 117, Feb. 1995, pp. 59-63.
Pech, P. et al., "Attenuation Values, Volume Changes and Artifacts in Tissue Due to Freezing," Acta Radiologica ,vol. 28, Issue 6, 1987, pp. 779-782.
Peterson, L. J. et al., "Bilateral Fat Necrosis of the Scrotum," Journal of Urology, vol. 116, 1976, pp. 825-826.
Phinney, S. D. et al., "Human Subcutaneous Adipose Tissue Shows Site-Specific Differences in Fatty Acid Composition," The American Journal of Clinical Nutrition, vol. 60, 1994, pp. 725-729.
Pierard, G.E. et al., "Cellulite: From Standing Fat Herniation to Hypodermal Stretch Marks," The American Journal of Dermatology, vol. 22, Issue 1, 2000, pp. 34-37, [Abstract].
Pope, K. et al. "Selective Fibrous Septae Heating: An Additional Mechanism of Action for Capacitively Coupled Monopolar Radiofrequency" Thermage, Inc. Article, Feb. 2005, 6pgs.
Quinn, P. J. "A Lipid-Phase Separation Model of Low-Temperature Damage to Biological Membranes," Cryobiology, 22, 1985, 128-146.
Rabi, T. et al., "Metabolic Adaptations in Brown Adipose Tissue of the Hamster in Extreme Ambient Temperatures," American Journal of Physiology, vol. 231, Issue 1, Jul. 1976, pp. 153-160.
Renold, A.E. et al. "Adipose Tissue" in Handbook of Physiology, Chapter 15, (Washington, D.C., 1965) pp. 169-176.
Rossi, A. B. R. et al. "Cellulite: a Review," European Academy of Dermatology and Venereology, 2000, pp. 251-262, 12 pgs.
Rubinsky, B. "Principles of Low Temperature Cell Preservation," Heart Failure Reviews, vol. 8, 2003, pp. 277-284.
Rubinsky, B. et al., "Cryosurgery: Advances in the Application of low Temperatures to Medicine," International Journal of Refrigeration, vol. 14, Jul. 1991, pp. 190-199.
Saleh, K.Y. et al., "Two-Dimensional Ultrasound Phased Array Design for Tissue Ablation for Treatment of Benign Prostatic Hyperplasia," International Journal of Hyperthermia, vol. 20, No. 1, Feb. 2004, pp. 7-31.
Schoning, P. et al., "Experimental Frostbite: Freezing Times, Rewarming Times, and Lowest Temperatures of Pig Skin Exposed to Chilled Air," Cryobiology 27, 1990, pp. 189-193.
Shephard, R. J. "Adaptation to Exercise in the Cold," Sports Medicine, vol. 2, 1985, pp. 59-71.
Sigma-Aldrich "Poly(ethylene glycol) and Poly(ethylene oxide)," http://www.sigmaaldrich.com/materials-science/materialscience-;products.htmi?TablePage=2020411 0, accessed Oct. 19, 2012.
Smalls, L. K. et al. "Quantitative Model of Cellulite: Three Dimensional Skin Surface Topography, Biophysical Characterization, and Relationship to Human Perception," International Journal of Cosmetic Science, vol. 27, Issue 5, Oct. 2005, 17 pgs.
Thermage, News Release, "Study Published in Facial Plastic Surgery Journal Finds Selective Heating of Fibrous Septae Key to Success and Safety of Thermage ThermaCool System," Jun. 20, 2005, 2 pages.
"ThermaCool Monopolar Capacitive Radiofrequency, The one choice for nonablative tissue tightening and contouring", Thermage, Inc. Tech Brochure, Nov. 30, 2005, 8 pgs.
Vallerand et al. "Cold Stress Increases Lipolysis, FFA Ra and TG/FFA Cycling in Humans," Aviation, Space, and Environmental Medicine 70(1), 1999, pp. 42-50.
Wang, X. et al., "Cryopreservation of Cell/Hydrogel Constructs Based on a new Cell-Assembling Technique," Sep. 5, 2009, 40 pages.
Wharton, D. A. et al., "Cold Acclimation and Cryoprotectants in a Freeze-Tolerant Antarctic Nematode, Panagrolaimus Davidi,", Journal of Comparative Physiology, vol. 170, No. 4, Mar. 2000, 2 pages.
Winkler, C. et al., "Gene Transfer in Laboratory Fish: Model Organisms for the Analysis of Gene Function," in Transgenic Animals, Generation and Use (The Netherlands 1997), pp. 387-395.
Young, H. E. et al. "Isolation of Embryonic Chick Myosatellite and Pluripotent Stem Cells" The Journal of Tissue Culture Methods, vol. 14, Issue 2, 1992, pp. 85-92.
Zelickson, B. et al., "Cryolipolysis for Noninvasive Fat Cell Destruction: Initial Results from a Pig Model", 35 Dermatol. Sug., 2009, pp. 1-9.
Zouboulis, C. C. et al., "Current Developments and Uses of Cryosurgery in the Treatment of Keloids and Hypertrophic Scars," Wound Repair and Regeneration, vol. 10, No. 2, 2002, pp. 98-102.
Examination Report for Brazilian Application No. PI 0701284-5; dated May 22, 2019; 9 pages.

\* cited by examiner

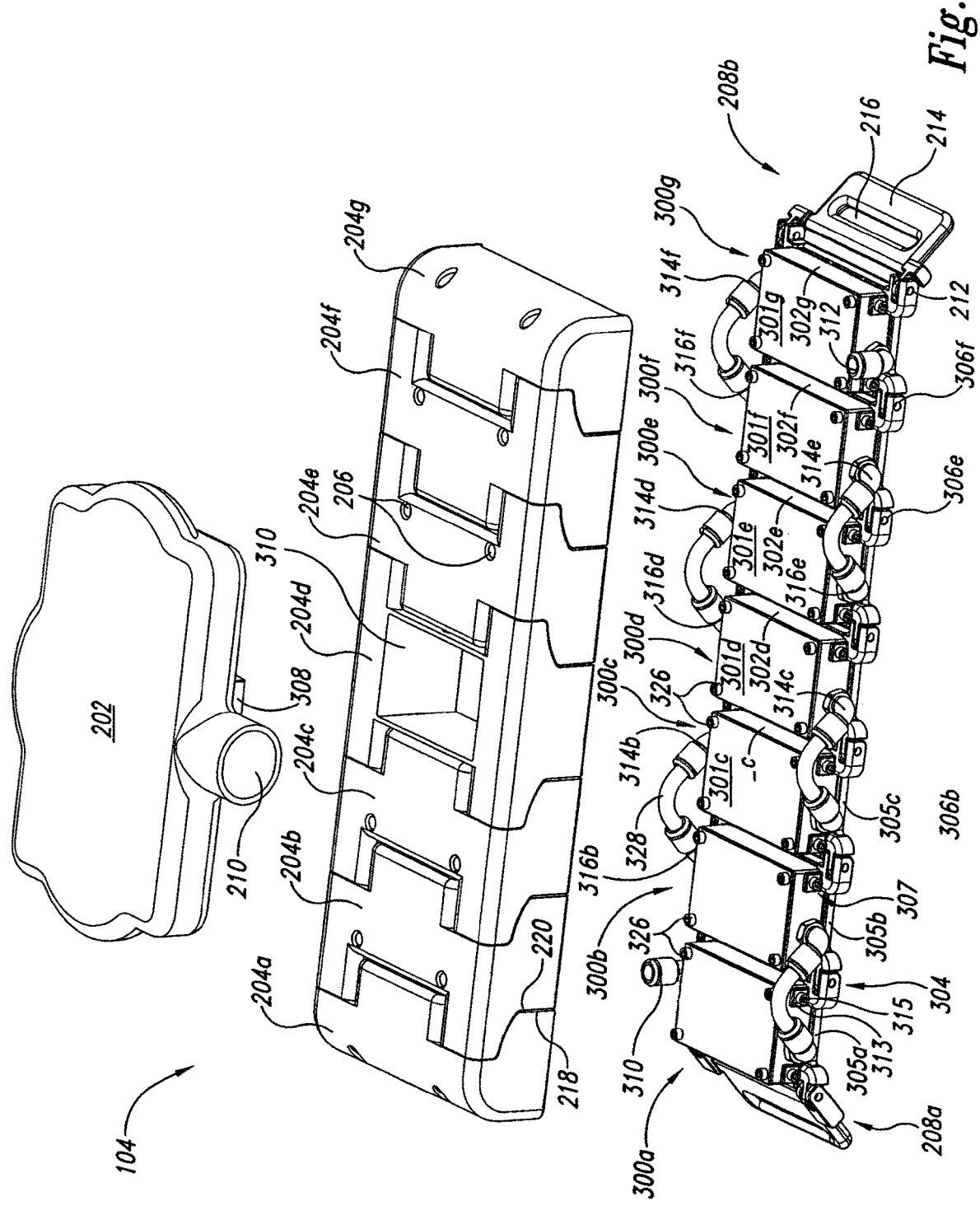

COOLING DEVICE HAVING A PLURALITY OF CONTROLLABLE COOLING ELEMENTS TO PROVIDE A PREDETERMINED COOLING PROFILE

CROSS-REFERENCE TO RELATED APPLICATIONS

The present application is a continuation of U.S. patent application Ser. No. 16/415,684, filed May 17, 2019, now U.S. Pat. No. 11,179,269, which is a continuation of U.S. patent application Ser. No. 14/825,841, filed Aug. 13, 2015, now U.S. Pat. No. 10,292,859, which is a continuation of U.S. patent application Ser. No. 13/616,186, filed Sep. 14, 2012, now U.S. Pat. No. 9,375,345, which is a continuation of U.S. patent application Ser. No. 11/528,225, filed Sep. 26, 2006, now U.S. Pat. No. 9,132,031. Each of these applications are incorporated herein by reference in their entireties.

TECHNICAL FIELD

The present application relates generally to cooling devices, systems, and methods for removing heat from subcutaneous lipid-rich cells, and more particularly, but not exclusively, to a cooling device having a plurality of controllable cooling elements to create a spatial cooling profile and/or a time-varying cooling profile in order to more efficiently affect subcutaneous lipid-rich cells.

BACKGROUND

Excess body fat increases the likelihood of developing various types of diseases such as heart disease, high blood pressure, osteoarthrosis, bronchitis, hypertension, diabetes, deep-vein thrombosis, pulmonary emboli, varicose veins, gallstones, hernias, and several other conditions.

In addition to being a serious health risk, excess body fat can also detract from personal appearance and athletic performance. For example, excess body fat can form cellulite, which causes an "orange peel" effect at the surface of the skin. Cellulite forms when subcutaneous fat protrudes into the dermis and creates dimples where the skin is attached to underlying structural fibrous strands. Cellulite and excessive amounts of fat are often considered to be unappealing. Thus, in light of the serious health risks and aesthetic concerns associated with excess fat, an effective way of controlling excess accumulation of body fat is urgently needed.

Liposuction is a method for selectively removing body fat to sculpt a person's body. Liposuction is typically performed by plastic surgeons and dermatologists using specialized surgical equipment that mechanically removes subcutaneous fat cells via suction. One drawback of liposuction is that it is a serious surgical procedure, and the recovery may be painful. Liposuction can have serious and occasionally even fatal complications. In addition, the cost for liposuction is usually substantial.

Conventional non-invasive treatments for removing excess body fat typically include topical agents, weight-loss drugs, regular exercise, dieting, or a combination of these treatments. One drawback of these treatments is that they may not be effective or even possible under certain circumstances. For example, when a person is physically injured or ill, regular exercise may not be an option. Similarly, weight-loss drugs or topical agents are not an option when they cause an allergic or negative reaction. Furthermore, fat loss in selective areas of a person's body cannot be achieved using general or systemic weight-loss methods.

Other non-invasive treatment methods include applying heat to a zone of subcutaneous lipid-rich cells. U.S. Pat. No. 5,948,011 discloses altering subcutaneous body fat and/or collagen by heating the subcutaneous fat layer with radiant energy while cooling the surface of the skin. The applied heat denatures fibrous septae made of collagen tissue and may destroy fat cells below the skin, and the cooling protects the epidermis from thermal damage. This method is less invasive than liposuction, but it still can cause thermal damage to adjacent tissue, and may be painful for the patient.

Another method of reducing subcutaneous fat cells is to cool the target cells as disclosed in U.S. Patent Publication No. 2003/0220674, the entire disclosure of which is incorporated herein. This publication discloses, among other things, reducing the temperature of lipid-rich subcutaneous fat cells to selectively affect the fat cells without damaging the cells in the epidermis. Although this publication provides promising methods and devices, several improvements for enhancing the implementation of these methods and devices would be desirable, including providing a plurality of controllable cooling elements to create a spatial cooling profile and/or a time-varying cooling profile in order to more efficiently affect subcutaneous lipid-rich cells.

U.S. Patent Publication No. 2003/0220674 also discloses methods for selective removal of lipid-rich cells and avoidance of damage to other structures including dermal and epidermal cells. A method for more efficiently and precisely controlling these effects is desirable. Therefore, a method for spatially cooling lipid-rich cells over a predetermined time-varying cooling profile, selected spatial cooling profile, or maintaining constant process parameters is also needed.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

FIG. 3 is an exploded isometric view of the cooling device of FIG. 2A for removing heat from subcutaneous lipid-rich cells in accordance with an embodiment of the invention.

DETAILED DESCRIPTION

A. Overview

Figure 1:
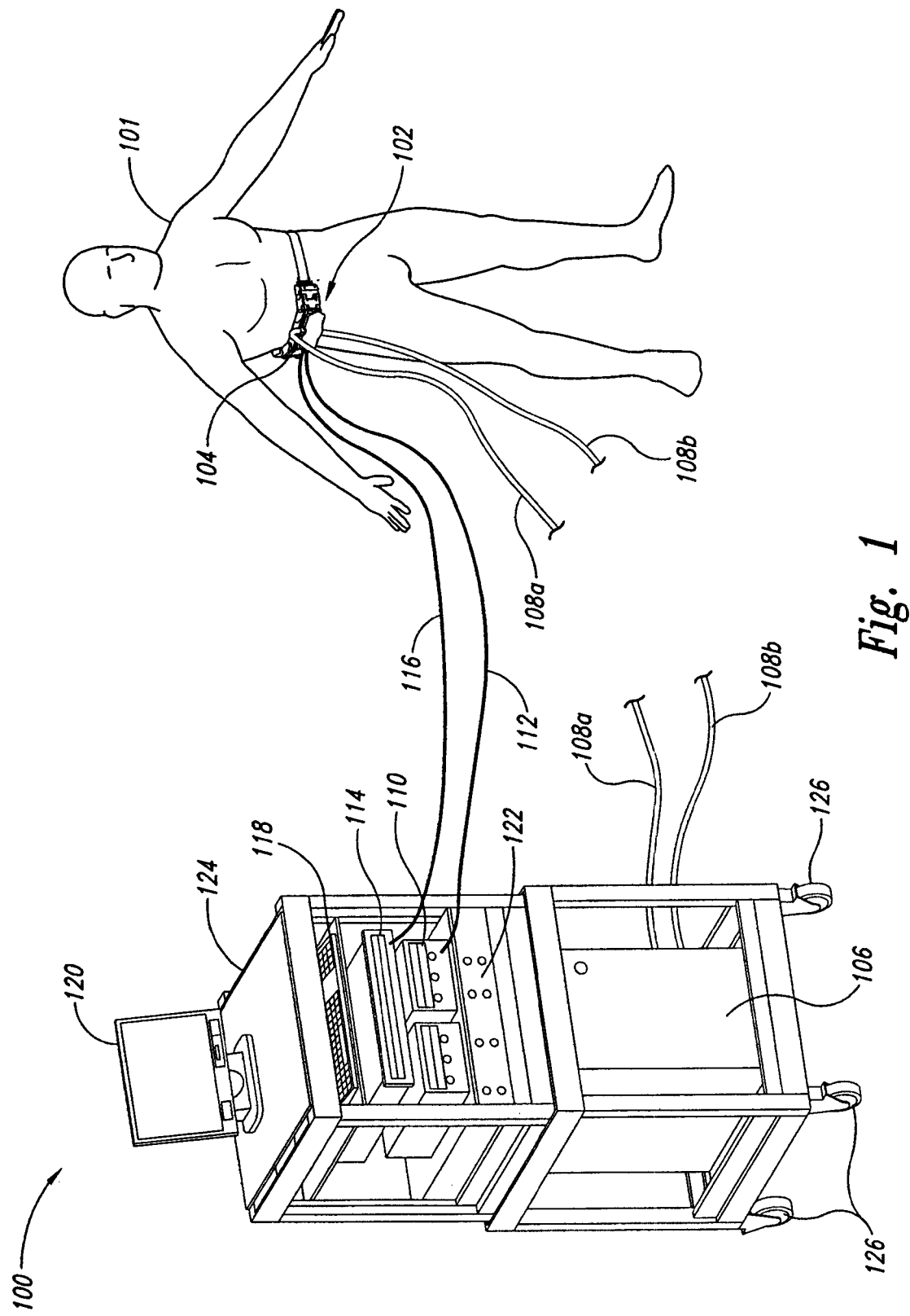
FIG. 1 is an isometric view of a system for removing heat from subcutaneous lipid-rich cells in accordance with an embodiment of the invention.

The present disclosure describes devices, systems, and methods for cooling subcutaneous lipid-rich cells. The term "subcutaneous tissue" means tissue lying underneath the dermis and includes adipocytes (fat cells) and subcutaneous fat. It will be appreciated that several of the details set forth below are provided to describe the following embodiments in a manner sufficient to enable a person skilled in the relevant art to make and use the disclosed embodiments. Several of the details and advantages described below, however, may not be necessary to practice certain embodiments of the invention. Additionally, the invention can include other embodiments that are within the scope of the claims but are not described in detail with respect to FIGS. 1-11.

Reference throughout this specification to "one embodiment" or "an embodiment" means that a particular feature, structure, or characteristic described in connection with the embodiment is included in at least one embodiment of the present invention. Thus, the occurrences of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the claimed invention.

The present invention is directed toward a cooling device for removing heat from subcutaneous lipid-rich cells of a subject. The cooling device includes a plurality of cooling elements movable relative to each other so as to be conformable to the skin of the subject.

One aspect is directed toward a cooling device for removing heat from subcutaneous lipid-rich cells. The cooling device includes a plurality of cooling elements contained within interconnected frame members rotatable about at least one axis, a plurality of heat exchanging elements, and a housing. Alternatively, the cooling device includes a plurality of cooling elements contained on a flexible substrate. The cooling elements can use a number of cooling technologies including, for example, thermoelectric coolers, recirculating chilled fluid, vapor compression elements, or phase change cryogenic devices. One skilled in the art will recognize that there are a number of other cooling technologies that could be used and that the cooling elements need not be limited to those described here.

Another aspect is directed toward a cooling device having a plurality of cooling members using thermoelectric Peltier principles or other cooling technologies. The cooling device also includes a heat dissipating member in thermal communication with the cooling members and a plurality of interface members having heat exchanging surfaces configured to contact a subject's skin. The cooling members can be capable of reducing a temperature of a region such that lipid-rich cells in the region are affected while non-lipid-rich cells are not generally affected.

Further aspects include that the cooling device can include a plurality of interconnected hinged segments for rotating to conform to a body portion. Alternatively, the cooling elements may also be disposed on a flexible substrate and movable relative to each other.

Another aspect is directed toward a cooling device having a plurality of cooling members individually controlled to provide a spatial cooling profile and/or a time-varying cooling profile. The cooling profile can, for example, be configured to provide cooling members along a perimeter of the cooling device at a lower or a higher temperature than cooling members at an interior of the cooling device. Alternatively, the cooling profile can be configured to provide cooling members in regions of the cooling device at a lower or a higher temperature than cooling members in adjacent regions of the cooling device. Further aspects include that the cooling profile can vary over time to provide a decreasing or an increasing temperature profile during treatment.

Another aspect is directed toward a method of applying a cooling device having a plurality of cooling elements contained on a plurality of interconnected hinged segments, each adjacent pair of hinged cooling elements being rotatable about at least one axis. The cooling elements can have a plurality of heat exchanging surfaces capable of removing heat from the subject's skin. The method includes rotating hinged segments containing the cooling elements to achieve a desired configuration of the cooling device, cooling the heat exchanging surfaces of the plurality of cooling elements to a desired temperature, placing the plurality of cooled heat exchanging surfaces proximate to the subject's skin, and reducing the temperature of a region such that lipid-rich cells in the region are affected while non-lipid-rich cells in the region are not generally affected. Alternatively, the cooling elements may be disposed on a flexible substrate and movable relative to each other.

Further aspects include a method for applying and maintaining pressure on the contact region. Further aspects include securing the cooling device in position with a retention device. Further aspects include providing a time-varying profile to increase or decrease the temperature of the cooling elements over a selected time period. Further aspects include spatially varying the temperature of each cooling element of the cooling device to provide discrete cooling regions in the cooling device.

Another aspect is directed toward a system for removing heat from subcutaneous lipid-rich cells. The system includes a cooling device having a plurality of frame segments containing cooling elements movable relative to each other, the frame segments capable of achieving a desired orientation between each other, and a heat sink coupled to the cooling device to dissipate heat generated by the cooling device. In one embodiment, the frame segments are hinged. When placed proximate to a subject's skin, the plurality of cooling elements can be capable of reducing a temperature of a region such that lipid-rich cells in the region are affected while non-lipid-rich cells in the epidermis and/or dermis are not generally affected.

Further aspects include the cooling device being configured to follow the contours of the body. Further aspects include that the cooling device includes a handle and/or can include a strap or other retention device for holding the cooling device in a selected position. Further aspects include a control system for individually controlling the temperature of the cooling elements in a predetermined pattern. Further aspects include a processing unit for controlling a time-varying cooling profile of the cooling device.

B. System for Selectively Reducing Lipid-Rich Cells

FIG. 1 is an isometric view of a system 100 for removing heat from subcutaneous lipid-rich cells of a subject 101 in accordance with an embodiment of the invention. The system 100 can include a cooling device 104 placed at an abdominal area 102 of the subject 101 or another suitable area for removing heat from the subcutaneous lipid-rich cells of the subject 101. Various embodiments of the cooling device 104 are described in more detail below with reference to FIGS. 2-11.

The system 100 can further include a cooling unit 106 and supply and return fluid lines 108a-b connecting the cooling device 104 to the cooling unit 106. The cooling unit 106 can remove heat from a coolant to a heat sink and provide a chilled coolant to the cooling device 104 via the fluid lines 108a-b. Examples of the circulating coolant include water, glycol, synthetic heat transfer fluid, oil, a refrigerant, and any other suitable heat conducting fluid. The fluid lines 108a-b can be hoses or other conduits constructed from polyethylene, polyvinyl chloride, polyurethane, and other materials that can accommodate the particular circulating coolant. The cooling unit 106 can be a refrigeration unit, a cooling tower, a thermoelectric chiller, or any other device capable of removing heat from a coolant. Alternatively, a municipal water supply (i.e., tap water) can be used in place of the cooling unit.

As explained in more detail below, the cooling device 104 includes a plurality of thermoelectric cooling elements, such as Peltier-type thermoelectric elements, which can be individually controlled to create a custom spatial cooling profile and/or a time-varying cooling profile. The system 100 can further include a power supply 110 and a processing unit 114 operatively coupled to the cooling device 104. In one embodiment, the power supply 110 can provide a direct current voltage to the thermoelectric cooling device 104 to effectuate a heat removal rate from the subject 101. The processing unit 114 can monitor process parameters via sensors (not shown) placed proximate to the cooling device 104 through power line 116 to adjust the heat removal rate based on the process parameters. The heat transfer rate can be adjusted to maintain constant process parameters. Alternately, the process parameters can vary either spatially or temporally. The processing unit 114 can be in direct electrical communication through line 112, or alternatively, may be connected via a wireless communication. Alternatively, the processing unit 114 can be preprogrammed to provide a spatially distributed cooling profile and/or a time-varying cooling profile. The processing unit 114 can include any processor, Programmable Logic Controller, Distributed Control System, and the like.

In another aspect, the processing unit 114 can be in electrical communication with an input device 118, an output device 120, and/or a control panel 122. The input device 118 can include a keyboard, a mouse, a touch screen, a push button, a switch, a potentiometer, and any other device suitable for accepting user input. The output device 120 can include a display screen, a printer, a medium reader, an audio device, and any other device suitable for providing user feedback. The control panel 122 can include indicator lights, numerical displays, and audio devices. In alternative embodiments, the control panel 122 can be contained on the cooling device 104. In the embodiment shown in FIG. 1, the processing unit 114, power supply 110, control panel 122, cooling unit 106, input device 118, and output device 120 are carried by a rack 124 with wheels 126 for portability. In alternative embodiments, the processing unit 114 can be contained on the cooling device 104. In another embodiment, the various components can be fixedly installed at a treatment site.

C. Cooling Device Having a Plurality of Cooling Elements

Figure 2A:
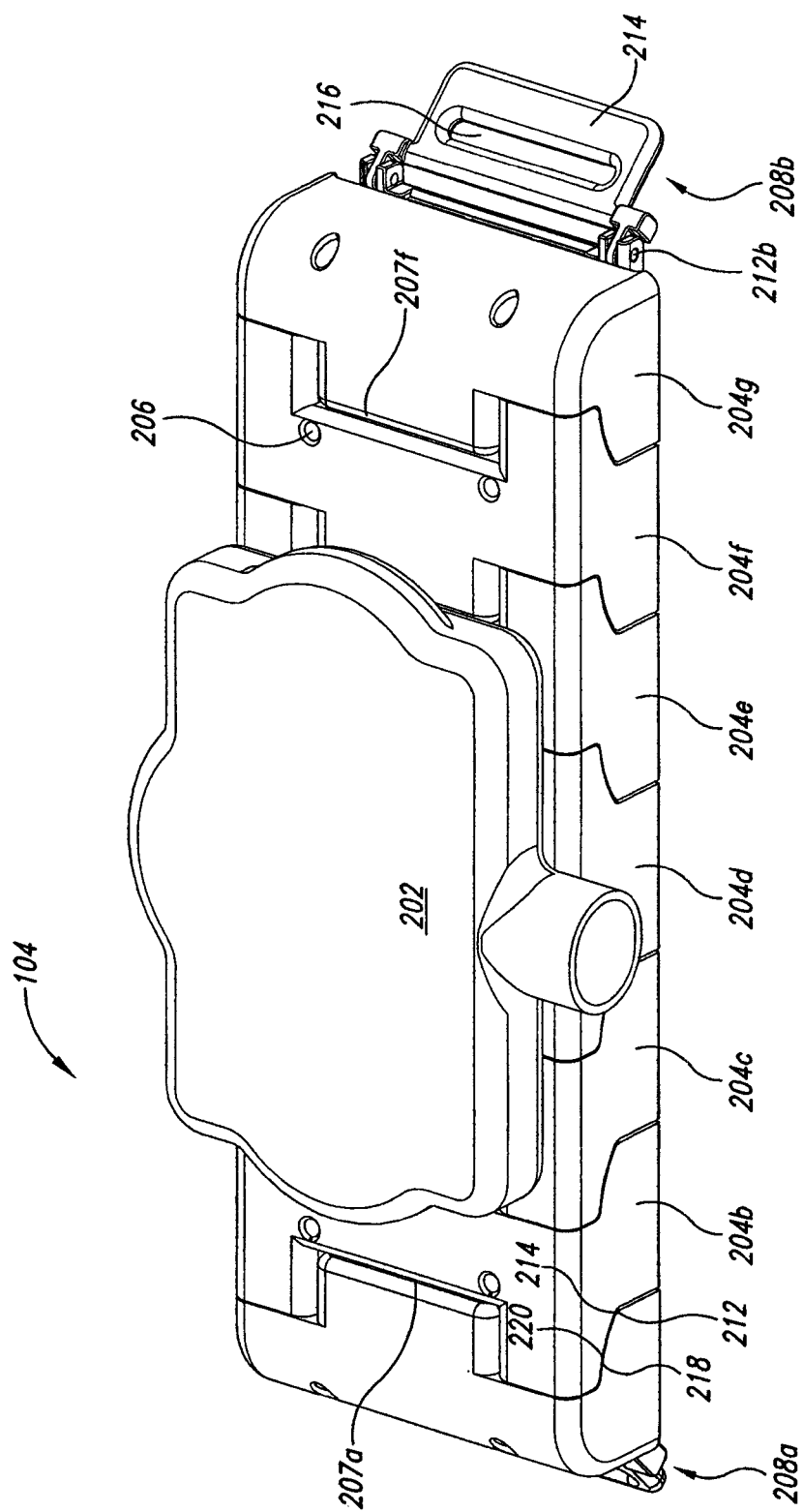
FIGS. 2A, 2B, 2C, and 2D are isometric views of a cooling device for removing heat from subcutaneous lipid-rich cells in accordance with embodiments of the invention.
Figure 2B:
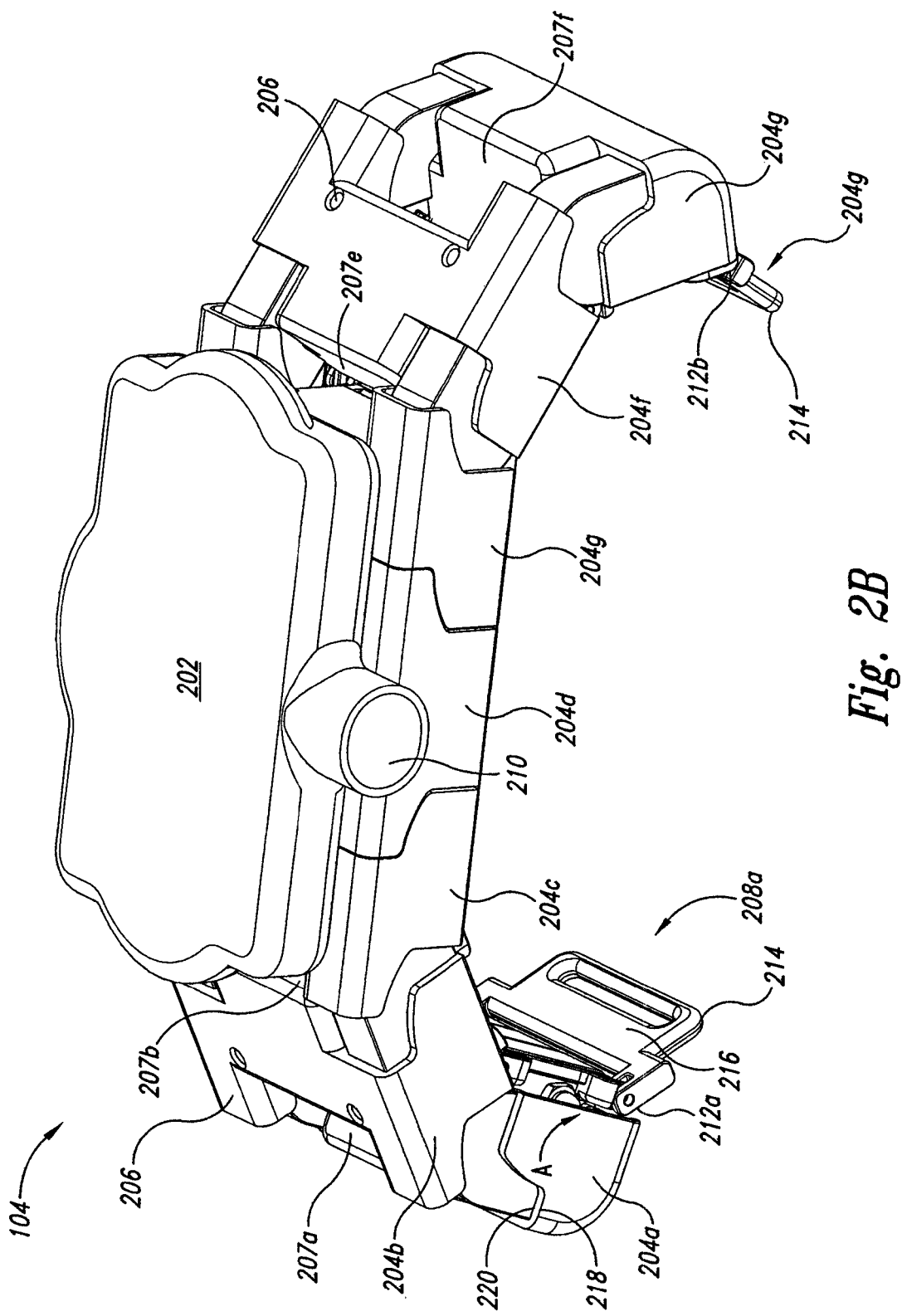
Figure 2C:
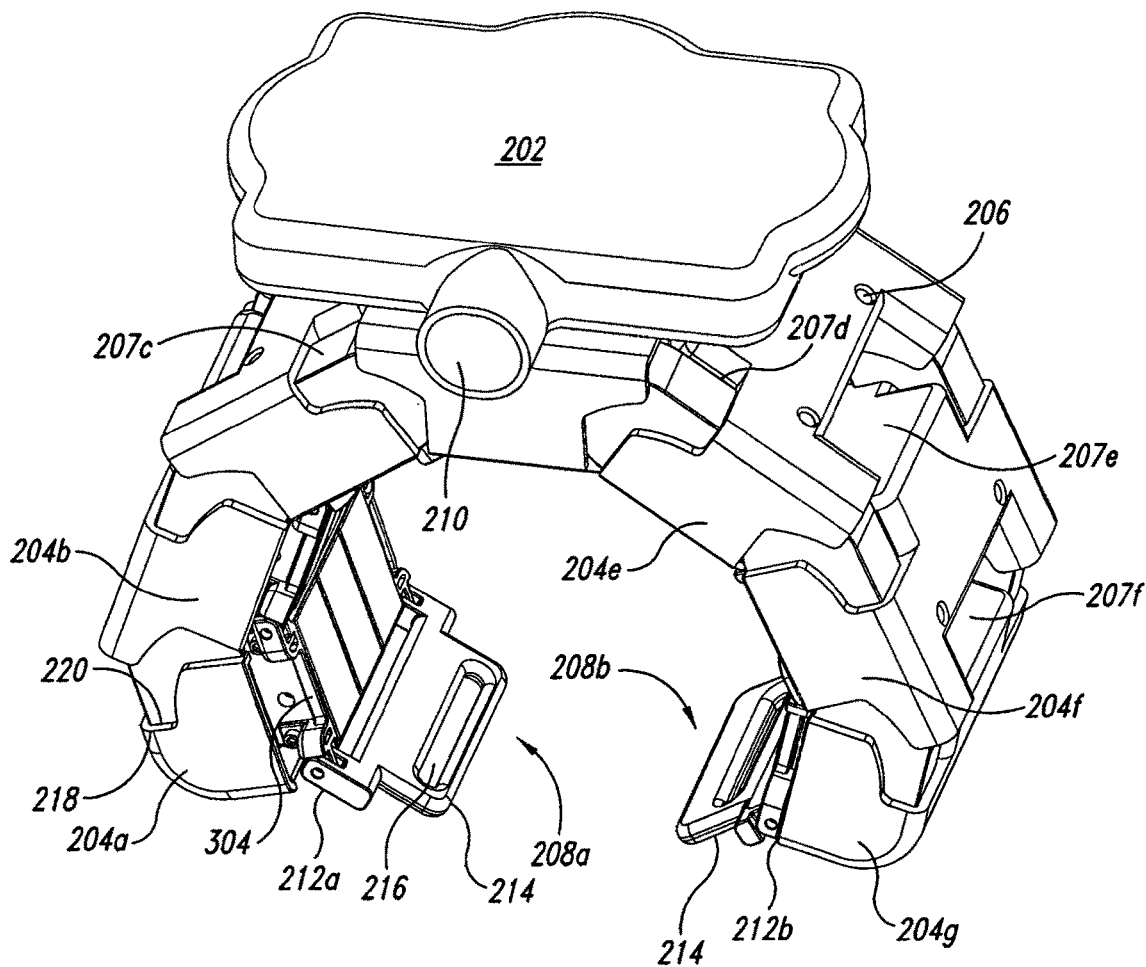

FIGS. 2A, 2B, and 2C are isometric views of a cooling device 104 in accordance with embodiments of the invention suitable for use in the system 100. In this embodiment, the cooling device 104 includes a control system housing 202 and cooling element housings 204a-g. The control system housing 202 includes a sleeve 308 (FIG. 3) that may slide into collar 310 and/or may mechanically attach to the cooling element housings. The cooling element housings 204a-g are connected to the heat exchanging elements (not shown) by attachment means 206. The attachment means can be any mechanical attachment device such as a screw or pin as is known in the art. The plurality of cooling element housings 204a-g can have many similar features. As such, the features of the first cooling element housing 204a are described below with reference symbols followed by an "a," corresponding features of the second cooling element housing 204b are shown and noted by the same reference symbol followed by a "b," and so forth. The cooling element housing 204a can be constructed from polymeric materials, metals, ceramics, woods, and/or other suitable materials. The example of the cooling element housing 204a shown in FIG. 2A-C is generally rectangular, but it can have any other desired shape.

The cooling device 104 is shown in a first relatively flat configuration in FIG. 2A; in a second slightly curved configuration in FIG. 2B; and in a third curved configuration in FIG. 2C. As shown in FIGS. 2B and 2C, each segment of the cooling element housings 204a-g are rotatably connected to adjacent segments and moveable about connection 207a-f to allow the cooling device 104 to curve. The connection 207a-f, for example, can be a pin, a ball joint, a bearing, or other type of rotatable joints. The connection 207 can accordingly be configured to rotatably couple the first cooling element housing 204a to the second cooling element housing 204b. According to aspects of the invention, the first cooling element housing 204a can rotate relative to the second cooling element housing 204b (indicated by arrow A), each adjacent moveable pair of cooling elements being such that, for example, the angle between the first and second cooling element housings 204a and 204b can be adjusted up to 45°. In this way, the cooling device is articulated such that it can assume a curved configuration as shown in FIG. 2B or 2C, conformable to the skin of a subject.

One advantage of the plurality of rotatable heat exchanging surfaces is that the arcuate shape of the cooling device may concentrate the heat transfer in the subcutaneous region. For example, when heat exchanging surfaces are rotated about a body contour of a subject, the arcuate shape can concentrate heat removal from the skin.

The control system housing 202 can house a processing unit for controlling the cooling device 104 and/or fluid lines 108*a-b* and/or electrical power and communication lines. The control system housing 202 includes a harness port 210 for electrical and supply fluid lines (not shown for purposes of clarity). The control system housing 202 can further be configured to serve as a handle for a user of the cooling device 104. Alternatively, the processing unit may be contained at a location other than on the cooling device.

As shown in FIGS. 2A, 2B, and 2C, the cooling device 104 can further include at each end of the cooling device 104 retention devices 208*a* and 208*b* coupled to a frame 304. The retention devices 208*a* and 208*b* are rotatably connected to the frame by retention device coupling elements 212*a-b*. The retention device coupling elements 212*a-b*, for example, can be a pin, a ball joint, a bearing, or other type of rotatable joints. Alternatively, the retention devices 208*a* and 208*b* can be rigidly affixed to the end portions of the cooling element housings 204*a* and 204*g*. Alternately, the retention device can attach to control system housing 202.

The retention devices 208*a* and 208*b* are each shown as tabs 214, each having a slot 216 therein for receiving a band or elastomeric strap (not shown for purposes of clarity) to retain the cooling device 104 in place on a subject 101 during treatment. Alternatively, the cooling device may not contain any attached retention device and may be held in place by hand, may be held in place by gravity, or may be held in place with a band, elastomeric strap, or non-elastic fabric (e.g., nylon webbing) wrapped around the cooling device 104 and the subject 101.

As shown in FIGS. 2A-2C, the cooling element housings 204*a-g* have a first edge 218 and an adjacent second edge 220 of a reciprocal shape to allow the cooling device 104 to mate and, thus, configure in a flat configuration. The first edge 218 and the second edge 220 are generally angular in the Figures; however, the shape could be curved, straight, or a combination of angles, curves, and straight edges that provide a reciprocal shape between adjacent segments of the cooling element housings 204*a-g*.

Figure 2D:
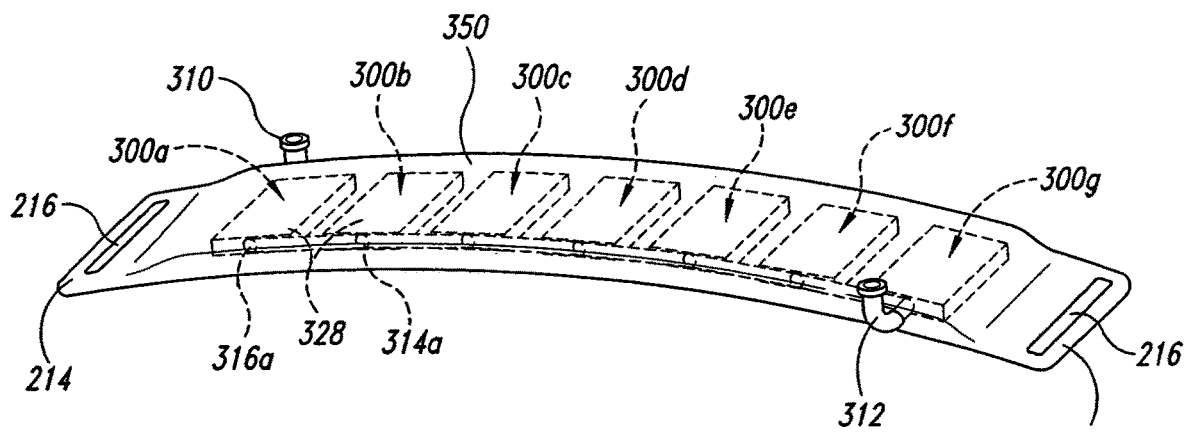

FIG. 2D shows an isometric view of an alternative cooling device 104 in accordance with embodiments of the invention suitable for use in the system 100. In this embodiment, the cooling device 104 includes a plurality of heat exchanging elements 300*a-g* contained within a flexible substrate 350. As described with respect to FIGS. 2A-2C, adjacent heat exchanging elements 300*a-g* are fluidically coupled in series by fluid lines 328.

According to aspects of the embodiment, the cooling elements 302*a-g* may be affixed to the flexible substrate 350, or may be embedded in the flexible substrate 350. The flexible substrate 350 can be constructed from polymeric materials, elastomeric materials, and/or other suitable materials. The flexible substrate 350 can further be an elastomer such as silicone or urethane or can be a fabric, such as nylon. The flexible substrate 350 can also be a thin polymer such as polypropylene or ABS. The example of the flexible substrate 350 shown in FIG. 2D is generally rectangular, but can have any other desired shape, including a matrix configuration or an anatomy specific shape. According to aspects of this embodiment, the flexible substrate 350 acts as a living hinge between cooling elements 302*a-g* to allow the cooling elements 302*a-g* to conform to the skin of a subject.

FIG. 3 is an exploded isometric view of a cooling device 104 in accordance with one embodiment of the invention suitable for use in the system 100. In this embodiment, the cooling device 104 includes a frame 304 having a plurality of rotatably connected segments 305*a-g*. The rotatably connected segments 305*a-g* are connected by hinges 306*a-g*. Alternatively, the rotatably connected segments 305*a-g* of the frame 304 could be connected by a connection that allows rotation, such as a pin, living hinge, flexible substrate, such as webbing or fabric, or the like. According to one aspect of the invention, the links or hinges are made of plastic to insulate the cooling elements from each other.

A plurality of heat exchanging elements 300*a-g* are contained on the frame 304. The heat exchanging elements 300*a-g* include cooling elements 302*a-g* having covers 301*a-g*. The covers 301*a-g* are affixed on a top side of the cooling elements 302*a-g*. The covers 301*a-g* may be affixed by various mechanical means as described further herein and as are known in the art. According to aspects of the invention, the covers 301*a-g* are fluidicly sealed to the cooling elements 302*a-g*. According to further aspects of the invention, the hinges 306*a-g* are configured so as to be adjacent to the subject's skin, in use, to maintain close proximity between the heat exchanging elements 300*a-g* when the heat exchanging elements 300*a-g* are in a rotated position.

The cooling elements 302*a-g* are attached by cooling element attachment means 307 to the frame 304 such that the first heat exchanging element 300*a* is located at the first segment 305*a* of the frame 304 and the second heat exchanging element 300*b* is located at the second segment 305*b* of the frame 304. The cooling element attachment means 307 are shown as a tab 313 extending from the frame 304 and a screw 315 fixedly attaching the tab 313 of the frame 304 to the cooling elements 302*a-g*. Alternatively, mechanical fixation devices as are known in the art may be used.

The cooling elements 302*a-g* of the cooling device 104 are generally configured to rotate to allow the cooling device 104 to conform to an arcuate portion of a subject 101. Once positioned on a subject 101, the cooling device 104 can further be strapped to or otherwise configured to be releasably attached to the subject 101. The cooling elements 302*a-g* can be configured to move relative to each other or rotate to position the cooling elements 302*a-g* for applying pressure to the treatment area during operation. Cooling elements 302*a-g* are movable or rotatable relative to each other such that cooling device 104 is conformable to the skin of the subject. These features are described in more detail below with reference to specific examples of the cooling devices.

The first cooling element 302*a* can include the cooling element housing 204*a*, a fluid inlet port 310 and a fluid outlet port 316*a*. The fluid inlet port 310 is fluidically coupled to the supply fluid line 108*a*. As shown in FIG. 3, adjacent cooling elements are fluidicly coupled in series by fluid lines 328 at fluid inlet ports 314*a-f* and fluid outlet ports 316*a-f*. The cooling element 302*g* further includes a fluid outlet port 312 fluidicly coupled to the return fluid line 108*b*.

One expected advantage of providing cooling elements fluidicly coupled in series is a uniform flow rate through each cooling element 302*a-g* to provide more consistent cooling of the cooling device. Another expected advantage of providing cooling elements 302*a-g* fluidicly coupled in series is fewer supply lines into the cooling device to provide a more reliable, less cumbersome and easier to house fluid flow configuration for the cooling device.

Figure 4:
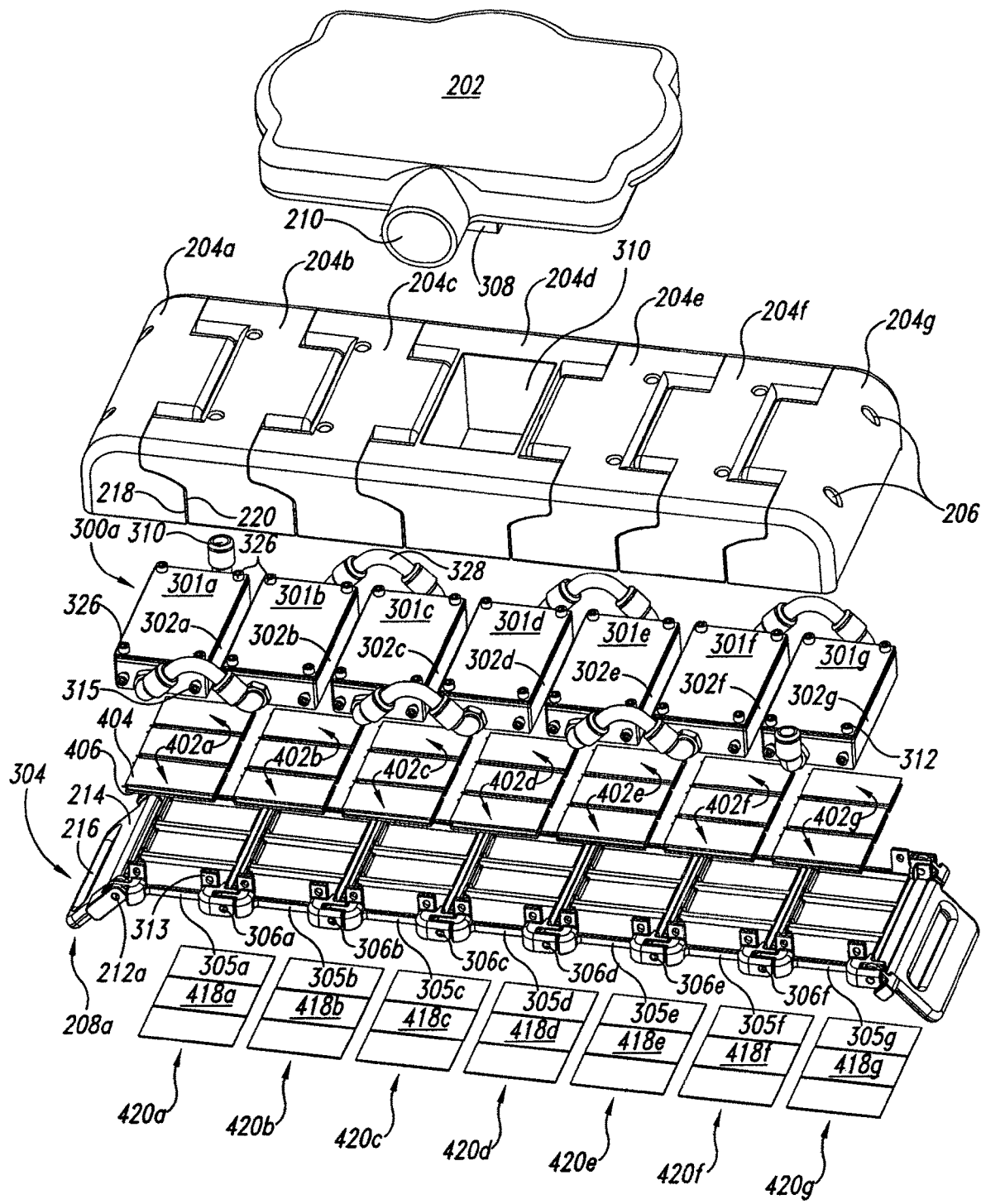
FIG. 4 is a further exploded isometric view of the cooling device of FIG. 3 illustrating additional components of the cooling device in accordance with another embodiment of the invention.

FIG. 4 is a further exploded isometric view of the cooling device of FIG. 3 in accordance with one example of the invention for use in the system 100. This further exploded view is substantially similar to previously described examples, and common acts and structures are identified by the same reference numbers. Only significant differences in operation and structure are described below. The cooling device 104 includes cooling elements 302*a-g* having a plurality of thermoelectric coolers 402 configured to reduce the temperature of a subcutaneous region of the subject 101 for selectively affecting lipid-rich cells in the region. The plurality of thermoelectric coolers 402, also known as a Peltier-type element, has a first side 404 and a second side 406. The first side 404 is in thermal communication with the cooling element 302, and the second side 406 is in thermal communication with an interface member 418. The thermoelectric coolers 402 can be connected to an external power supply (not shown) to transfer heat between the first side 404 and the second side 406. One suitable thermoelectric cooler is a Peltier-type cooling element (model #CP-2895) produced by TE Technologies, Inc. in Traverse City, Mich.

The thermoelectric coolers 402 are contained within the segments 305a-g of the frame 304. According to aspects of the invention, the frame 304 may contain individual guides for each thermoelectric cooler 402. Alternatively, the thermoelectric coolers 402 may be retained on the cooling elements 302a-g, for example, by thermal epoxy or by a combination of solder, mechanical compression and thermal grease.

As shown in FIG. 4, the plurality of cooling elements 302a-g can further include a plurality of interface members 418 in thermal communication with the thermoelectric cooler 402 having heat exchanging surfaces 420 for transferring heat to/from the subject 101. In one example, the interface members 418 are generally planar, but in other examples, the interface members 418 are non-planar (e.g., curved, faceted, etc.) The interface members 418 can be constructed from any suitable material with a thermal conductivity greater than 0.05 Watts/Meter Kelvin, and in many examples, the thermal conductivity is more than 0.1 Watts/Meter Kelvin. Examples of suitable materials include aluminum, other metals, metal alloys, graphite, ceramics, some polymeric materials, composites, or fluids contained in a flexible membrane.

By applying power to the thermoelectric coolers 402, heat can be effectively removed from the subject's skin to a circulating fluid in cooling elements 302a-g. For example, applying a current to the thermoelectric coolers 402 can achieve a temperature generally below 37° C. on the first side 404 of the thermoelectric coolers 402 to remove heat from the subject 101 via the interface members 418. The thermoelectric coolers 402 pull heat from the second side 406 to the first side 404 where the heat is then transferred to the circulating fluid. The cooling unit 106 then removes the heat from the circulating fluid.

The thermoelectric coolers 402 can be configured to withdraw a sufficient amount of heat quickly from the subject 101 without using a high-current power supply for the cooling unit 106. In order to facilitate thermal transfer, the interface members 418 can be an aluminum plate configured generally the same dimensions at the thermoelectric coolers 402. According to aspects of the invention, the thermoelectric coolers 402 can be Peltier-type thermoelectric elements rated at about 160 watts. As such, the cooling device 104 can cool a portion of the subject's skin from a temperature of about 37° C. to about −20° C. quickly and effectively. The cooling unit 106 can use a normal voltage power supply (e.g., 120 VAC) because the power consumption is not excessive. This enables the system to be used in hospitals, clinics, and small offices without more costly high voltage electrical systems.

Figure 5A:
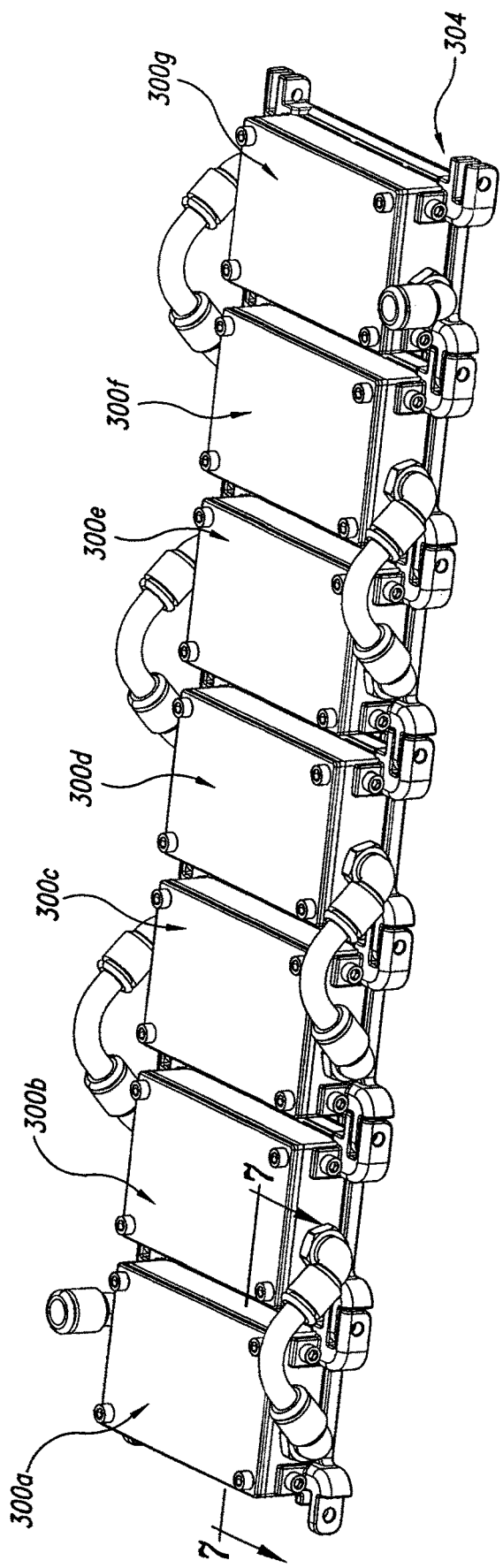
FIG. 5A is an isometric view of a plurality of heat exchangers connected in series in accordance with another embodiment of the invention.

FIG. 5A is an isometric view of a plurality of heat exchanging elements 300a-g connected in series with the housing removed to better show the plurality of heat exchanging elements 300a-g and interconnected fluid lines. According to aspects of the invention, the heat exchanging elements 300a-g are rotatably contained on linked segments of the frame 304 to provide a cooling device that is wider than it is tall. Thus, the cooling device is compliant and will form to follow contours. According to aspects of the invention, the cooling device is dimensionally small in a first dimension so that curvature of the treatment area in a second dimension does not significantly impact the amount of surface area in contact between the skin and the cooling device.

Figure 5B:
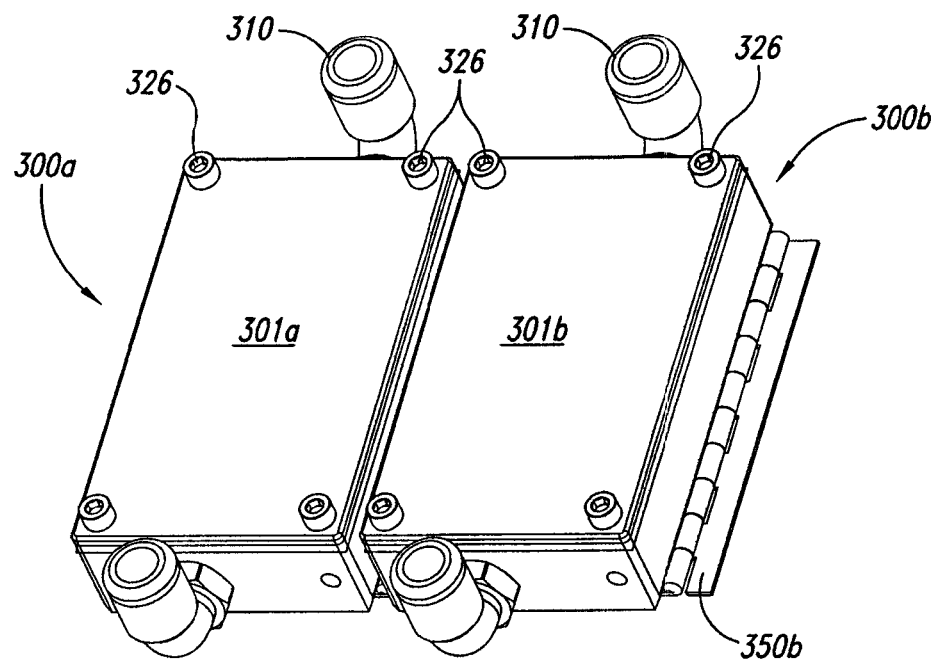
FIG. 5B is an isometric top view of a plurality of heat exchangers connected in series in accordance with yet another embodiment of the invention.
Figure 5C:
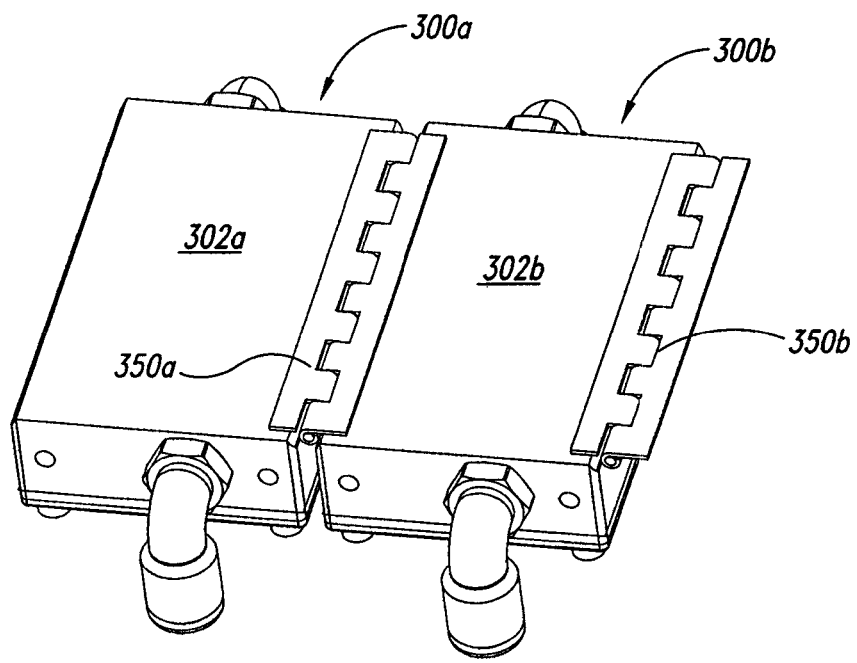
FIG. 5C is an isometric bottom view of the heat exchangers in FIG. 5B.

According to further embodiments of the invention, FIG. 5B is an isometric top view of a plurality of heat exchangers connected in series by a hinge 350a, 350b, wherein the hinge connection is connected directly to the heat exchanger 302a, 302b. The hinge 350a, 350b as shown in FIG. 5B is a piano hinge that extends along adjacent edges of the heat exchanger 300a, 300b for the length of the heat exchanger 300a, 300b, alternatively, the hinge 350a, 350b may extend a portion of the length of the adjacent sides of the heat exchanger 300a, 300b or the hinged connection may include a plurality of hinges 350a 350b. Unlike in FIG. 5A, no frame is employed to connect the heat exchangers 300a, 300b or provide support for the hinged connection between heat exchangers 300a, 300b. FIG. 5C is an isometric bottom view of the heat exchangers in FIG. 5B. According to further aspects of the invention, alternative hinged mechanical connections as is known in the art may be used alone or in combination; or, alternative chemical connections such as flexible adhesives or a living hinge as is known in the art may be used in the hinged connections; or, electromechanical connections such as magnets may be used between heat exchangers to connect the heat exchangers.

Figure 6A:
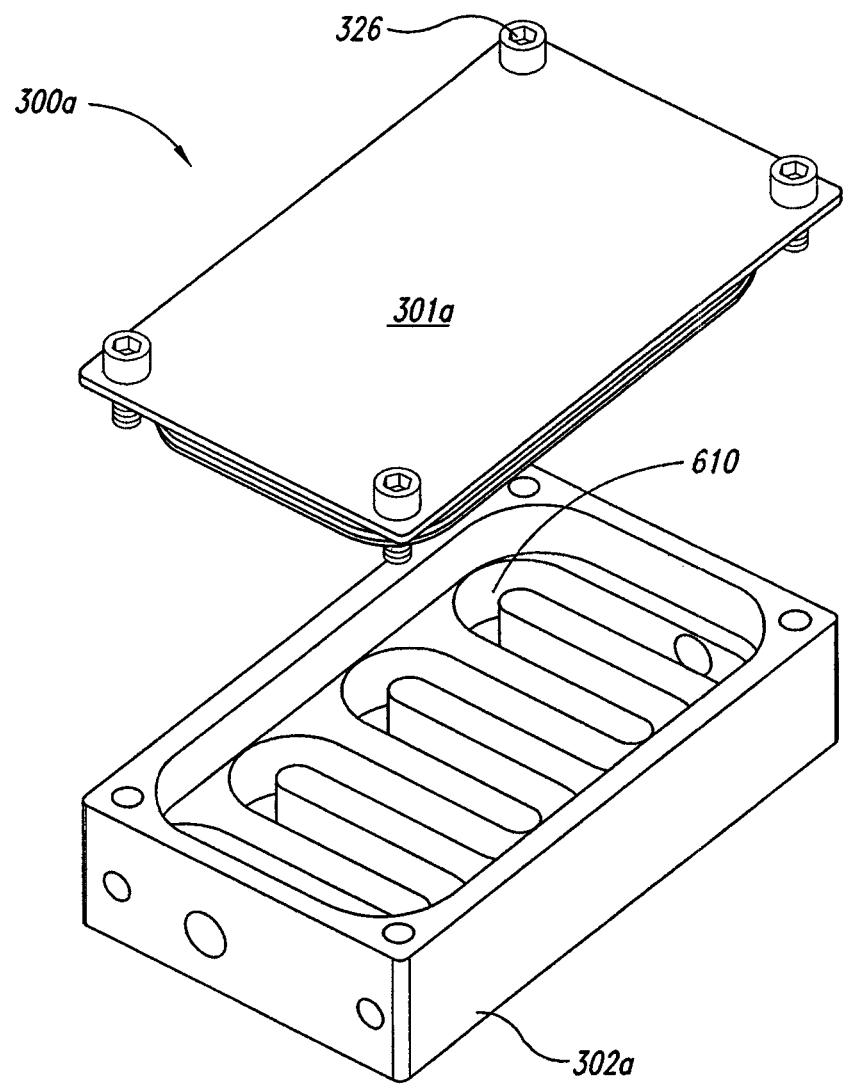
FIG. 6A is an exploded isometric view of one of the heat exchangers shown in FIG. 5A.
Figure 6B:
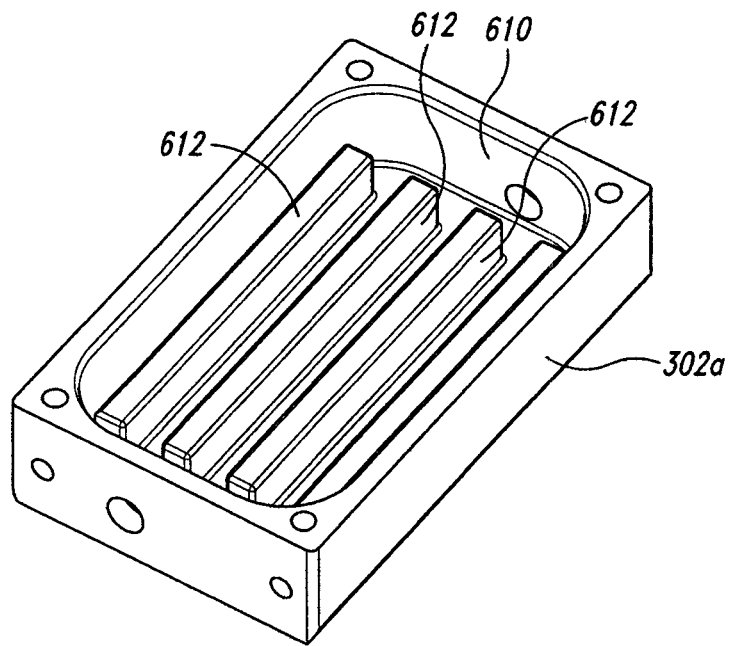
FIG. 6B is an isometric view of an alternative configuration of a cooling element of a heat exchanger in accordance with an embodiment of the invention.

FIG. 6A is an exploded isometric side elevation view of the heat exchanging element 300a shown in FIG. 5A to further show the flow of fluid in the heat exchanging element 300a. Like reference symbols refer to like features and components in the Figures. As shown in FIG. 6A, the heat exchanging element 300a can include a fluid chamber 610 having a serpentine shape within the cooling element 302a. As shown in FIG. 6B, the heat exchanging element 300a can include fins 612 to direct fluid flow through the fluid chamber 610. The fluid chamber 610 can be in fluid communication with the associated fluid ports such that fluid can circulate through the fluid chamber 610. The fluid chamber 610 can be configured to accept fluid coolants, such as water, glycol, a synthetic heat transfer fluid, oil, refrigerants, air, carbon dioxide, nitrogen, and argon. According to further aspects of the invention, the fluid chamber 610 may be configured in a variety of configurations as is known in the art in order to distribute the fluid throughout the cooling element 302a.

Figure 7:
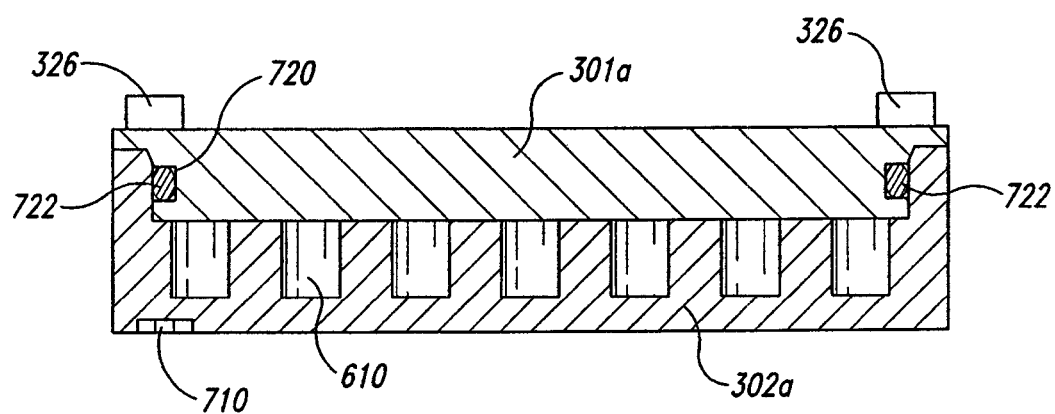
FIG. 7 is a cross-sectional view of one of the cooling elements along line 7-7 of FIG. 5A.

FIG. 7 is a cross-sectional view of one cooling element 302a. The cooling element 302a is fluidicly sealed by cover 301a containing an o-ring seal 722, held in place by an attachment means 326. According to aspects of the invention, the cooling element 302a can further include at least one sensing element 710 proximate to the heat exchanging surface 420 (FIG. 4). The sensing element 710, for example, can be generally flush with the heat exchanging surface 420. Alternatively, it may be recessed or protrude from the surface. The sensing element 710 can include a temperature sensor, a pressure sensor, a transmissivity sensor, a bioresistance sensor, an ultrasound sensor, an optical sensor, an infrared sensor, a heat flux sensor, or any other desired sensor as described further herein.

In one example, the sensing element 710 can be a temperature sensor configured to measure the temperature of the first heat exchanging surface 420 and/or the temperature of the skin of the subject 101. For example, the temperature sensor can be configured as a probe or as a needle that penetrates the skin during measurement. Examples of suitable temperature sensors include thermocouples, resistance temperature devices, thermistors (e.g., neutron-transmutation-doped germanium thermistors), and infrared radiation temperature sensors. In another example, the sensing element 710 can be an ultrasound sensor configured to measure crystallization or change in viscosity of subcutaneous fat in the treatment region of a subject. In yet another example, the sensing element 710 can be an optical or infrared sensor configured to monitor an image of the treatment region to detect, for example, epidermal physiological reactions to the treatment. The sensing element 710 can be in electrical communication with the processing unit 114 via, for example, a direct wired connection, a networked connection and/or a wireless connection.

Accordingly, the cooling device 104 can be in electrical communication with the processing unit 114, and the cooling temperature can be automatically adjusted by the processing unit 114. According to further aspects of the invention, the temperature of the interface member 418 can be sensed by the sensing element 710 and the sensed electrical signal can be converted by the processing unit 114 into a process value for the temperature. In one embodiment, the processing unit 114 can include a Proportional, Integral and Derivative controller, which can adjust the power output to the thermoelectric coolers 402 to achieve and/or maintain the desired temperature.

According to further aspects of the invention, the sensing element 710 can alternatively be a pressure sensor to sense the pressure exerted by the cooling element 302a against the subject 101. In one embodiment, the interface member 418 can be attached to the frame 304 such that pressure applied against the heat exchanging element 300a is transferred via the housing 204a to the pressure sensor. The pressure sensor can alternatively be configured to sense the pressure in the fluid chamber 610 for monitoring pressure variations in the fluid chamber 610. Alternatively, the pressure could be inferred from force and the known contact area of the cooling elements. For example, the sensing element 710 can be any type of load-sensitive pressure sensing element such as a load cell (model #LC201-25) produced by OMEGA Engineering, Inc. in Stamford, Conn. Direct pressure measurement could also be performed by placing a pressure measurement membrane directly at the interface between the cooling element and the skin.

The cooling elements 302a-g can have many additional embodiments with different and/or additional features without detracting from the operation of the elements. For example, an adjacent cooling element may or may not have a sensing element proximate to the heat exchanging surface. Alternatively, the cooling elements can be constructed from a material that is different from that of the adjacent cooling element.

Figure 8:
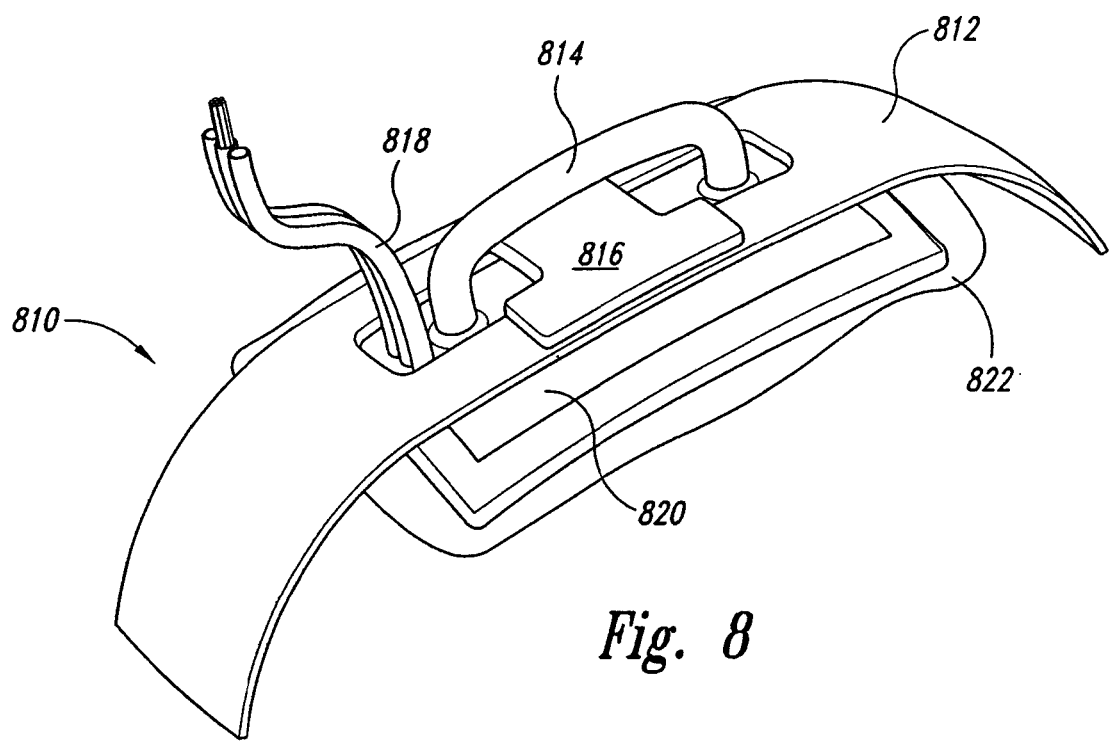
FIG. 8 is an isometric top view of an alternative cooling device for removing heat from subcutaneous lipid-rich cells in accordance with an embodiment of the invention.
Figure 9:
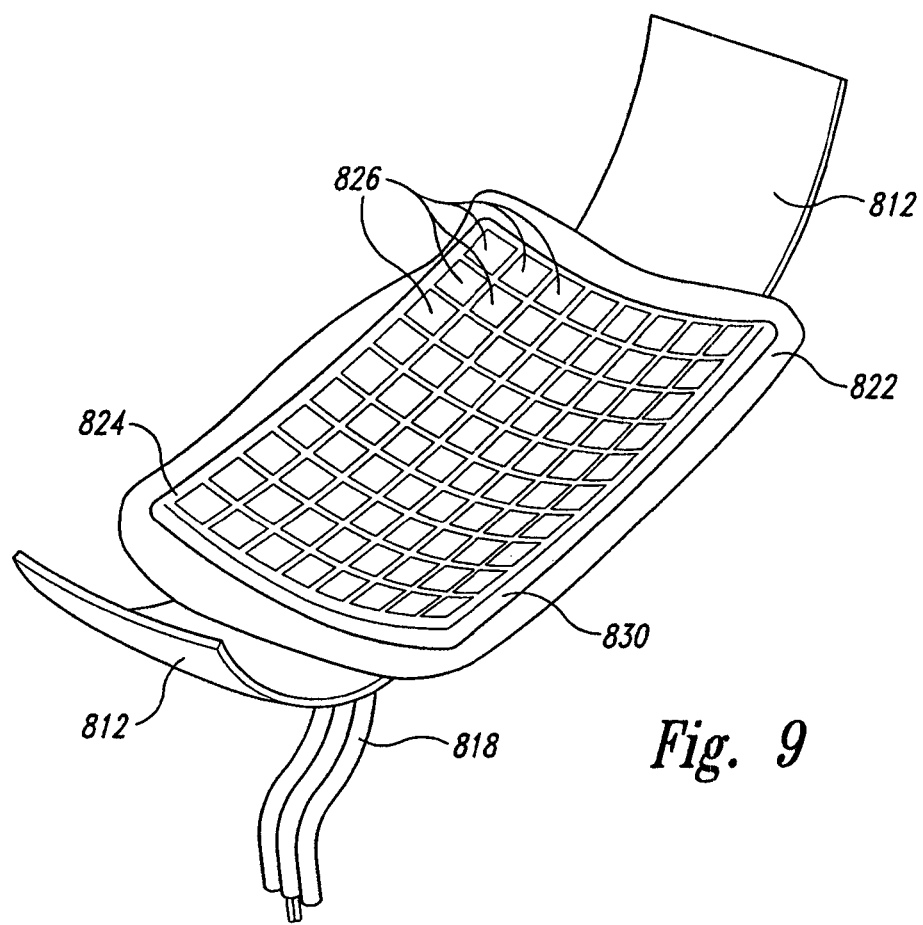
FIG. 9 is an isometric bottom view of the alternative cooling device of FIG. 8.

FIG. 8 shows an isometric view of a plurality of thermoelectric coolers contained in a matrix design. FIGS. 8 and 9 are isometric views of an alternative cooling device for removing heat from subcutaneous lipid-rich cells in accordance with an embodiment of the invention. As shown in FIGS. 8 and 9, the cooling device 810 includes a cooling element 804 configured in a planar matrix. The cooling device 810 can include a band 812 for retaining the cooling element 804 in place during use. The cooling device can further include a handle 814, a wiring harness 818 and a flap 816 for releasably securing the band 812 to the cooling element 804. The cooling element 804 can further include a sleeve 822 as described further above.

As shown in FIG. 9, the cooling element 804 includes a planar matrix 824 including a plurality of thermoelectric coolers 826. The thermoelectric coolers 826 are contained on a flexible substrate 830. The flexible substrate 830 can be an elastomer such as silicone or urethane or can be a fabric, such as nylon. According to further aspects, the flexible substrate 830 can be a thin polymer such as polypropylene or ABS. As described in greater detail herein, the thermoelectric coolers 826 can have small protective interface plates (not shown) glued to the cold surface of the thermoelectric coolers 826 with a thermal epoxy. According to alternative embodiments of the invention, additional mechanical restraints can further be included in the flexible substrate 830 to capture the thermoelectric coolers 826. As described in greater detail herein, the thermoelectric coolers 826 can include a heat exchanger (shown and described with respect to FIGS. 3-7) on the hot side to cool the hot side. According to aspects of this embodiment, each thermoelectric cooler 826 can have a corresponding heat exchanger to provide increased flexibility to the planar matrix. Alternately, a single flexible heat exchanger can be coupled to the hot side of the thermoelectric coolers (e.g., a bladder or other flexible membrane that water can be circulated through).

According to alternative aspects of the embodiment, the planar matrix 824 can further include temperature or other sensors (not shown) captured between the interface plate and the thermoelectric coolers and/or can have a separate sleeve that houses temperature sensors as further discussed herein.

D. Operation of the Cooling Device

Figure 10:
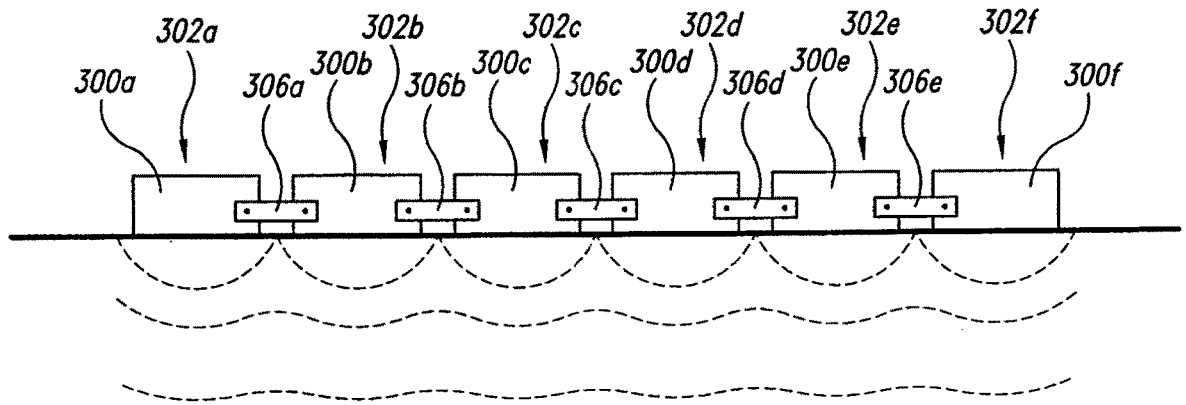
FIG. 10 is an exemplary sectional view of a lateral cooling pattern in the dermis of the skin in accordance with another embodiment of the invention.

FIG. 10 is an exemplary sectional view of a lateral cooling pattern in the dermis of the skin. The cooling pattern radiates from the cooling elements 302a-f through the epidermis and dermis of the skin such that when it affects the targeted dermis layer containing the lipid-rich cells, the cooling pattern forms a uniform cooling layer and any gaps between the segments of the frame are mitigated. One expected advantage of this cooling pattern is that the cooling of the dermis layer is uniform during treatment. FIG. 10 discloses cooling device 104 applied to a generally flat portion of a subject's body. Cooling elements 302a-f of the cooling device are movable relative to each other (as shown in FIGS. 2B, C and D), to conform to the contours of the subject's skin.

Without being bound by theory, it is believed that, in operation, effective cooling from the cooling device 104, which cools through conduction, depends on a number of factors. Two exemplary factors that impact heat removal from the skin area are the surface area of the cooling element and the temperature of the interface member. When conduction is between two materials that are placed in physical contact, i.e., the skin and the cooling element, there is a certain amount of thermal resistance known as contact resistance. The contact resistance takes the form of a temperature differential between the two materials. Higher contact resistance means less effective cooling; therefore, in the cooling device it is desirable to minimize contact resistance.

One means to minimize contact resistance and maximize the contact surface area is with an interface member that is flexible and will conform to the natural body contours. According to alternative aspects, contact pressure can be reduced by increasing the pressure of the applicator on the skin. Surface pressure has an additional benefit in a skin cooling application. Sufficient pressure on the skin can cause internal capillaries to constrict, temporarily reducing the flow of blood into the treatment region. Reduced blood flow into the treatment area allows the area being cooled to cool more efficiently and improves the effectiveness of the treatment.

Thus, according to aspects of the invention, the cooling device also incorporates a flexible strapping material or belt that wraps around the subject following the curvature of the cooling device. By tightening the strapping, pressure is applied and can be maintained between the subject and the cooling device. According to aspects of the invention, the strap can incorporate a hoop or d-ring through which the strapping can be looped to provide mechanical advantage in tightening the strap. According to further aspects of the invention, the strap also incorporates Velcro or a latch or buckle to hold the pressure once the strap has been tightened.

In operation, an operator can hold the cooling device 104 in one hand by grasping the control system housing 202 or another type of suitable handle (not shown). Then the cooling elements 302*a-g* can be moved or rotated to achieve a desired orientation. The operator can place the cooling device 104 having the cooling elements 302*a-g* in the desired orientation proximate to the subject's skin to remove heat from a subcutaneous region of the subject 101. In one embodiment, the operator tightens retention devices 208*a-b* affixed to the cooling device 104 to apply pressure to the subject's skin. In another embodiment, the operator can manually press the cooling device 104 against the subject's skin. The operator can also monitor and control the treatment process by collecting measurements, such as skin temperatures, from the sensing element 710. By cooling the subcutaneous tissues to a temperature lower than 37° C., more preferably lower than 25° C., subcutaneous lipid-rich cells can be selectively affected. The affected cells are then resorbed into the patient through natural processes.

According to aspects of the invention, interface members 418, for example thin aluminum plates, are mounted to the bottom of the thermoelectric coolers in a manner to ensure good thermal contact between the thermoelectric coolers and the interface members. The interface members can be coupled to the cooling element by a variety of mechanical fixation means such as are known in the art. For example, the coupling means can include using thermally conductive epoxy or using thermal grease such as zinc oxide.

In operation, cooling is efficiently distributed through the heat exchanging elements 300*a-g*. For example, the cooling device includes a series of interface members 418 approximately 1 mm in thickness. The interface members 418 are in thermal communication with the cooling elements 302*a-g* by mechanical fixation such as thermal epoxy. The cooling elements 302*a-g* are cooled by a plurality of thermoelectric coolers to provide a more efficient cooling system to the treatment region. The cooling elements 302*a-g* are contained on segments that are movable relative to each other to conform to the contours of the subject's skin. Alternatively, the cooling elements are rotatable relative to each other, similar to the joined segments of a metal watch band, thus allowing the assembly to curve.

As designed, the interface members and cooling elements protect the thermoelectric coolers while maintaining good heat transfer between the thermoelectric coolers and the skin. The interface members are sized such that they do not present a significant thermal mass. In one design, each thermoelectric cooler could be 1"×1.5". The interface member or aluminum plate could also be 1"×1.5" with a thickness of 0.04". If the thermoelectric coolers' cooling power is approximately 10 W, which is appropriate based on the heat flux expected to conduct from the skin, then the aluminum plate would cool from an ambient temperature of 20° C. to a treatment temperature of −10° C. in about 7 seconds. The change in internal energy of the plate is described by the following equation:

$$\Delta E = \rho \cdot V \cdot C \cdot \Delta T$$

where $\Delta E$ is the change in internal energy, $\rho$ is the material density, $V$ is the material volume, $C°$ is the heat capacity of the material, and $\Delta T$ is the temperature change. In the problem described above, the volume of the aluminum plate is $V=1$ in×1.5 in×0.04 in or 0.06 in$^3$ (9.8×10−7 m3). For a typical grade of aluminum, $C°=875$ J/kg*° C. and $\rho=2770$ kg/m3. Solving the equation using these constants:

$$\Delta E = 2770 \text{ kg/m3} * 9.8 \times 10^{-7} \text{ m3} * 875 \text{ J/kg} *° \text{C.} * 30° \text{C.} = 71.3 \text{ J}$$

If the thermoelectric coolers have a cooling power of 10 W, then 71.3 J could be removed from the aluminum plate in 7.1 seconds, as is shown in the calculation below:

$$71.3 \text{ J}/(10 \text{ J/second}) = 7.13 \text{ seconds}$$

A small gap or recess in the frame at the skin surface may be included in one embodiment. Prior to applying the cooling device to the skin, a thermally conducting fluid or coupling agent can be applied to the device and to the skin to minimize contact resistance and increase heat transfer between the cooling device and the skin. This coupling agent will fill the gap in the cooling device and allow for limited lateral conduction between the thermoelectric coolers' plates. This will create a more uniform temperature gradient across the surface area of the skin when the cooling is applied to the skin.

The coupling agent may be applied to the skin or to the interface member to provide improved thermal conductivity. The coupling agent may include polypropylene glycol, polyethylene glycol, propylene glycol, and/or glycol. Glycols, glycerols, and other deicing chemicals are efficient freezing-point depressants and act as a solute to lower the freezing point of the coupling agent. Propylene glycol (CH3CHOHCH2OH) is one exemplary component of deicer or non-freezing coupling agents. Other components include polypropylene glycol (PPG), polyethylene glycol (PEG), polyglycols, glycols, ethylene glycol, dimethyl sulfoxide, polyvinyl pyridine, calcium magnesium acetate, sodium acetate, and/or sodium formate. The coupling agent preferably has a freezing point in the range of −40° C. to 0° C., more preferably below −10° C. as further described in U.S. Provisional Application 60/795,799, entitled Coupling Agent For Use With a Cooling Device For Improved Removal of Heat From Subcutaneous Lipid-Rich Cells, filed on Apr. 28, 2006, herein incorporated in its entirety by reference.

One expected advantage of using the cooling device 104 is that subcutaneous lipid-rich cells can be reduced generally without collateral damage to non-lipid-rich cells in the same region. In general, lipid-rich cells can be affected at low temperatures that do not affect non-lipid-rich cells. As a result, lipid-rich cells, such as subcutaneous adipose tissue, can be affected while other cells in the same region are generally not damaged even though the non-lipid-rich cells at the surface are subject to even lower temperatures. Another expected advantage of the cooling device 104 is that it is relatively compact because the cooling device 104 can be configured as a handheld device. Yet another advantage is that the cooling device can be applied to various regions of the subject's body because the cooling elements 302*a-g* can be adjusted to conform to any body contour.

Another expected advantage is that by pressing the cooling device 104 against the subject's skin, blood flow through the treatment region can be reduced to achieve efficient cooling. Yet another expected advantage is the use of pressure by constriction of the band to restrict blood flow to the treatment region and thereby reduce heat transfer (by mass transport). Thus, the band can not only provide a means for holding the cooling element in place, but also ensures good thermal contact between the cooling device and the skin, and further constricts the flow of blood in the treatment region. Still another expected advantage is that the plurality of the cooling elements 302*a-g* more efficiently remove heat from the skin compared to a single cooling element.

E. Spatially Controlled Cooling Element Profile

Many skin cooling devices rely on a relatively thick piece of aluminum or other conductive material between a thermoelectric cooler or other cooling source and the skin. When a cooling device is applied to a relatively insulating material, such as skin tissue, the aluminum plate becomes isothermal and maintains a constant temperature profile across the skin's surface. The drawback of this design is that when the device initially cools, or during thermal cycling, the thermal mass presented by the aluminum plate requires a large cooling power. This either translates into increased cooling time or increased power required from the cooling device or both.

According to aspects of the invention, the cooling device has a low thermal mass that will still maintain a constant temperature profile across the skin's surface. Further, according to aspects of the invention, a plurality of cooling elements are provided to allow different regions of the skin to be treated at different temperatures during one treatment session. There are some circumstances where it may be desirable to cool different regions of the skin to different temperatures or for different time periods. According to aspects of the invention, each thermoelectric cooler can be individually controlled to cool different regions of the skin to different temperatures and/or for different time periods and/or to ensure uniform temperature throughout the treatment region. One reason this may be desirable is that the composition of tissue is different in different locations of the body. Some regions have thicker layers of adipose tissue than others, which influence the thermal response of the skin. In other regions, the presence of bone or other organs will affect the heat transfer to the skin.

According to aspects of the invention, a spatially controlled temperature profile can provide more efficient cooling to the treatment region. The plurality of thermoelectric coolers allows the cooling device to accommodate spatial cooling. For example, thermoelectric coolers contained at the perimeter of the cooling device may have a lower or higher temperature or duration than thermoelectric coolers contained at the interior of the cooling device because of different boundary conditions in the different areas of the treatment zone. According to aspects of the invention, the cooling device will quickly and efficiently cool skin to a prescribed temperature. In addition, the cooling device described here has the additional ability to treat a large area in a single treatment while cooling different regions to different temperatures and/or for different durations.

This variation in localized cooling could alternatively be achieved using a cooling device that is relatively small such that many treatments are performed, cooling to different temperatures in different regions. However, this type of cooling device would require many treatments, thereby increasing the overall treatment time and the opportunity for operator error. In addition, a cooling device with a large thermal mass would require a longer cooling time during each treatment.

According to aspects of the invention, the device can accommodate spatially controlled cooling temperature profiles which may provide at least the following advantages: (1) increased efficiency; (2) decreased power consumption with comparable efficacy; (3) increased patient comfort; or (4) decreased treatment time. For example, according to aspects of the invention, the plurality of thermoelectric coolers will allow adjustment for anatomical differences between patients by selectively enabling or disabling portions of the apparatus based on anatomical differences of the patient. One example includes disabling the thermoelectric coolers around bony anatomy for patient comfort or for power conservation.

Alternatively, a particular pattern of controlled cooling may be customized to match an individual patient's pattern of cellulite, thus increasing the efficacy of the treatment. Similarly, treatment regions requiring a higher intensity of treatment may be pre-identified by ultrasound or other devices. The device can then be spatially controlled to provide higher intensity treatment to pre-identified areas. Further advantages include increased patient comfort and safety by allowing spatial control of cooling to accommodate unnatural anatomy (e.g. lumps, blemishes, nipples, hairy areas, scars, wounds, presence of implants, jewelry, or areas of heightened sensitivity.)

A further advantage of spatial control of the device includes utilizing only a subset of the cooling elements in order to treat only the region requiring treatment. It is advantageous to use one device that can accommodate small and large treatment regions without over treating (e.g. a large device that cannot be spatially controlled) or having to move the device multiple times thus extending the treatment time (e.g. a treatment device smaller than the treatment region). Thus, according to aspects of the invention, a selected region of thermoelectric coolers can be controlled to a few degrees warmer than another region of thermoelectric coolers. Alternatively, a first region of the cooling device can be turned off while a second region of the cooling device is activated, such that only a selected region of the subject is treated, thus limiting the treatment region. Other advantageous spatially controlled patterns include treating areas within the treatment region more intensely, conserving power by alternating thermoelectric coolers, increasing cooling at a perimeter in order to provide a uniform cooling pattern across the treatment area, and a combination of these spatially controlled patterns in order to increase treatment efficacy, reduce treatment time, decrease power consumption and provide for patient comfort and safety.

F. Time-Varying Cooling Profiles

In certain embodiments, once a desired temperature is achieved, the temperature of the region can be maintained for a predetermined period of time. The cooling cycle can be terminated by separating the heat exchanging surfaces 420*a-g* from the skin. After a certain period of time, if desired, the cooling device 104 can be reapplied to the same portion of the skin as described above until the lipid-rich cells are affected an amount sufficient to produce a desired reduction in lipid-rich cells. In another embodiment, the cooling device 104 can be applied to a different portion of the skin as described above to selectively affect lipid-rich cells in a different subcutaneous target region.

Alternatively, the cooling elements 302*a-g* can be controlled according to a predetermined time-varying cooling profile to cool, heat, re-cool, and/or cool in a stepped temperature pattern over time. In particular, according to aspects of the invention, patterns of controlled cooling over time provide at least the following advantages: (1) increased efficiency; (2) decreased power consumption with comparable efficacy; (3) increased patient comfort; or (4) decreased treatment time. One exemplary cooling pattern includes cooling to −5° for 15 minutes, warming to 30° for 5 minutes, cooling to −3° for 10 minutes. According to aspects of the present invention, any desired time-varying cooling profile can be programmed into the device. For example, a gradual or stepped cooling rate may decrease power requirements. Alternatively, a rapid cooling rate may be used in order to supercool the treatment region. Exemplary cooling rates include 5 to 1000 degrees per minute, more preferably 30 to 120 degrees per minute, and most preferably 35 to 100 degrees per minute.

One expected advantage of controlling the time-temperature profile of the device is that in practice, tissue is sensitive to cooling rates and thus tissue damage can be controlled by controlling the rate of cooling of the treatment region. Further, cooling the treatment region down over an extended period of time, or in phases, will increase patient comfort.

Another expected advantage of several of the embodiments described above is that the cooling device 104 can selectively reduce subcutaneous lipid-rich cells without unacceptably affecting the dermis, epidermis, and/or other tissues. Another expected advantage is that the cooling device 104 can simultaneously selectively reduce subcutaneous lipid-rich cells while providing beneficial effects to the dermis and/or epidermis. These effects may include: fibroplasia, neocollagenesis, collagen contraction, collagen compaction, collagen density increase, collagen remodeling, and acanthosis (epidermal thickening). In the treatment of cellulite, it is expected that dermal thickening above the herniating superficial fat lobules will help reduce the appearance of cellulite and improve the longevity of the effect. Another expected advantage is that the cooling device 104 can conform to various body contours of a subject by rotating or moving the cooling elements 302a-g to achieve a desired orientation. Yet another expected advantage is that the cooling device 104 can be configured as a handheld device for ease of operation. Furthermore, another expected advantage is that the system 100 with the handheld cooling device 104 and the rack-mounted processing unit 114 and cooling unit 106 are compact and efficient such that the method described above can be administered in an outpatient clinic or a doctor's office instead of in a hospital. Yet another expected advantage is that the cooling device 104 can be strapped in place to free the clinician's hands and allow the clinician to do other tasks with the treatment is in process.

G. Method of Applying Cooling Devices with a Plurality of Rotatable or Movable Cooling Elements In operation, the angle between the heat exchanging surfaces 420 is selected by rotating or moving the cooling elements 302a-g. The angle between the cooling elements 320a-g is often selected to conform the heat exchanging surfaces 320a-g to various body contours of the subject 101 and/or a desired clamping arrangement. In the embodiment shown in FIG. 2A, the angle between the heat exchanging surfaces 320a-g can be generally 180°, i.e., the heat exchanging surfaces 320a-g are generally coplanar for applying the cooling device to a treatment region. In the embodiment shown in FIG. 2B, the angle can be less than 180° to allow the cooling device to curve about a subject's body. In the embodiment shown in FIG. 2C, the cooling device is further curved to conform to a subject's body. In other embodiments, the angle can be any angle to conform to a subject's body, as would be recognized by one skilled in the art.

After configuring the cooling elements 302a-g, an operator places the cooling device 104 proximate to the skin of the subject 101. In the embodiment shown in FIG. 2A (where the angle is in a generally flat configuration), the cooling elements 302a-g are initially placed flat against a subject's skin. The operator then rotates or moves the cooling device to conform to a subject's body. The cooling device can be tightened by a strap, and a pressure can be increased by tightening the strap further. Optionally, the pressure sensor can be used to sense the clamping pressure applied via the interface members 418, and the sensed clamping force can be processed by the processing unit 114 and displayed on the output device 120. The pressure can then be adjusted based on the displayed values. Depending on the location of the cooling device, the pressure, for example, can be higher than the systolic pressure in the skin to impede or block the blood flow into the treatment region. Applying such pressure enables more effective cooling of the target region because there is less blood flow to transfer core body heat to the treatment region.

Applying the cooling device with pressure to the subject's skin or pressing against the skin can be advantageous to achieve efficient cooling. In general, the subject 101 has a body temperature of about 37° C., and the blood circulation is one mechanism for maintaining a constant body temperature. As a result, blood flow through the dermis and subcutaneous layer of the region is a heat source that counteracts the cooling of the subdermal fat. As such, if the blood flow is not reduced, cooling the subcutaneous tissues would require not only removing the specific heat of the tissues but also that of the blood circulating through the tissues. Thus, reducing or eliminating blood flow through the treatment region can improve the efficiency of cooling and avoid excessive heat loss from the dermis and epidermis.

By cooling the subcutaneous tissues to a temperature lower than 37° C., subcutaneous lipid-rich cells can be selectively affected. In general, the epidermis and dermis of the subject 101 have lower amounts of unsaturated fatty acids compared to the underlying lipid-rich cells forming the subcutaneous tissues. Because non-lipid-rich cells usually can withstand colder temperatures better than lipid-rich cells, the subcutaneous lipid-rich cells can be selectively affected while maintaining the non-lipid-rich cells in the dermis and epidermis. An exemplary range for the cooling elements 302a-g can be from about −20° C. to about 20° C., preferably from about −20° C. to about 10° C., more preferably from about −15° C. to about 5° C., more preferably from about −10° C. to about 0° C.

The lipid-rich cells can be affected by disrupting, shrinking, disabling, destroying, removing, killing, or otherwise being altered. Without being bound by theory, selectively affecting lipid-rich cells is believed to result from localized crystallization of highly saturated fatty acids at temperatures that do not induce crystallization in non-lipid-rich cells. The crystals can rupture the bi-layer membrane of lipid-rich cells to selectively necrose these cells. Thus, damage of non-lipid-rich cells, such as dermal cells, can be avoided at temperatures that induce crystal formation in lipid-rich cells. Cooling is also believed to induce lipolysis (e.g., fat metabolism) of lipid-rich cells to further enhance the reduction in subcutaneous lipid-rich cells. Lipolysis may be enhanced by local cold exposure, inducing stimulation of the sympathetic nervous system.

H. Computing System Software Modules

Figure 11:
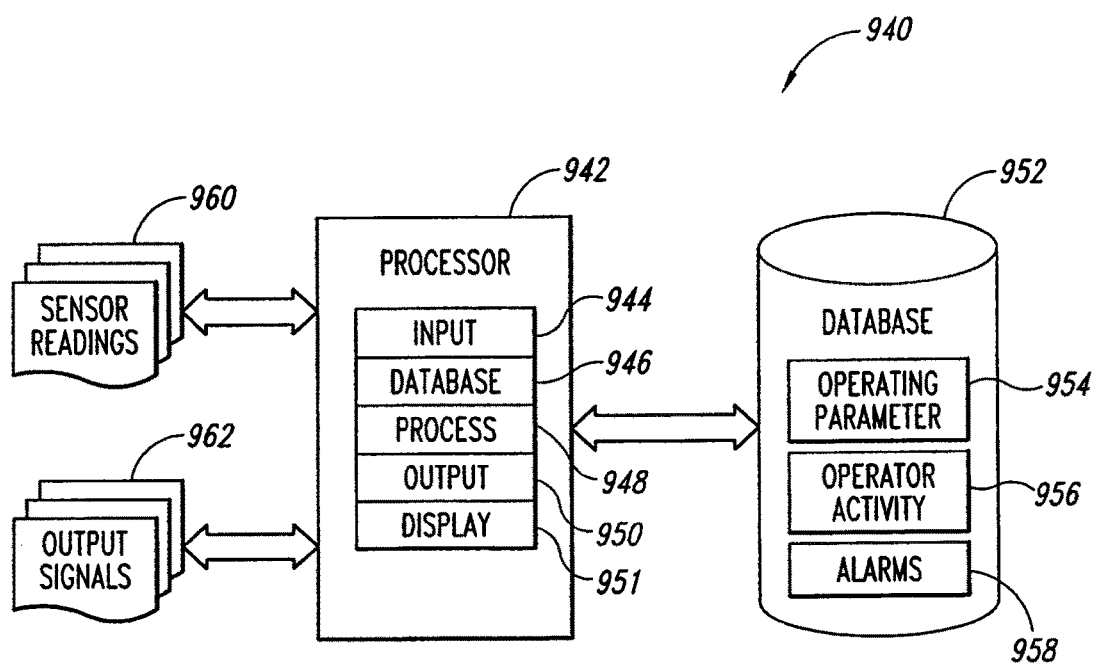
FIG. 11 is a block diagram showing computing system software modules for removing heat from subcutaneous lipid-rich cells in accordance with another embodiment of the invention.

FIG. 11 is a functional diagram showing exemplary software modules 940 suitable for use in the processing unit 114. Each component can be a computer program, procedure, or process written as source code in a conventional programming language, such as the C++ programming language, and can be presented for execution by the CPU of processor 942. The various implementations of the source code and object and byte codes can be stored on a computer-readable storage medium or embodied on a transmission medium in a carrier wave. The modules of processor 942 can include an input module 944, a database module 946, a process module 948, an output module 950, and, optionally, a display module 951. In another embodiment, the software modules 940 can be presented for execution by the CPU of a network server in a distributed computing scheme.

In operation, the input module 944 accepts an operator input, such as process setpoint and control selections, and communicates the accepted information or selections to other components for further processing. The database module 946 organizes records, including operating parameters 954, operator activities 956, and alarms 958, and facilitates storing and retrieving of these records to and from a database 952. Any type of database organization can be utilized, including a flat file system, hierarchical database, relational database, or distributed database, such as provided by a database vendor such as Oracle Corporation, Redwood Shores, Calif.

The process module 948 generates control variables based on sensor readings 960, and the output module 950 generates output signals 962 based on the control variables. For example, the output module 950 can convert the generated control variables from the process module 948 into 4-20 mA output signals 962 suitable for a direct current voltage modulator. The processor 942 optionally can include the display module 951 for displaying, printing, or downloading the sensor readings 960 and output signals 962 via devices such as the output device 120. A suitable display module 951 can be a video driver that enables the processor 942 to display the sensor readings 960 on the output device 120.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number, respectively. When the claims use the word "or" in reference to a list of two or more items, that word covers all of the following interpretations of the word: any of the items in the list, all of the items in the list, and any combination of the items in the list.

The above detailed descriptions of embodiments of the invention are not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. For example, while steps are presented in a given order, alternative embodiments may perform steps in a different order. The various embodiments described herein can be combined to provide further embodiments.

In general, the terms used in the following claims should not be construed to limit the invention to the specific embodiments disclosed in the specification, unless the above detailed description explicitly defines such terms. While certain aspects of the invention are presented below in certain claim forms, the inventors contemplate the various aspects of the invention in any number of claim forms. Accordingly, the inventors reserve the right to add additional claims after filing the application to pursue such additional claim forms for other aspects of the invention.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the invention can be modified, if necessary, to employ cooling devices with a plurality of cooling elements, thermally conductive devices with various configurations, and concepts of the various patents, applications, and publications to provide yet further embodiments of the invention.

These and other changes can be made to the invention in light of the above-detailed description. In general, in the following claims, the terms used should not be construed to limit the invention to the specific embodiments disclosed in the specification and the claims, but should be construed to include all cooling that operates in accordance with the claims. Accordingly, the invention is not limited by the disclosure, but instead its scope is to be determined entirely by the following claims.

We claim:

1. A cooling device for removing heat from subcutaneous lipid-rich cells of a subject having skin, the cooling device comprising:
   a body;
   a surface configured to face the subject's skin;
   an inlet port configured to be coupled to a supply line;
   an outlet port configured to be coupled to an output line; and
   a cooling element positioned along a flow path between the inlet and outlet ports such that liquid from the inlet port flows through the cooling element, the cooling element including:
      a thermoelectric cooler,
      an interface member made of a metal or metal alloy and having one or more heat exchanging surfaces,
      a serpentine shaped internal fluid chamber in thermal communication with the interface member and a plurality of fluid ports in fluid communication with opposite ends of the serpentine shaped internal fluid chamber, wherein the fluid ports are configured to allow the liquid to circulate in one direction through the serpentine shaped internal fluid chamber, wherein the liquid in communication with the serpentine shaped internal fluid chamber is circulated through a device that chills the liquid, wherein adjacent sections of the serpentine shaped internal fluid chamber are defined by a cover containing an o-ring, wherein the cooling element is attached to the body such that the one or more heat exchanging surfaces of the interface member form at least a temperature controlled portion of the surface configured to face the subject's skin and the thermoelectric cooler is within the body, and
      a sensing element proximate to the interface member; and
   wherein the cooling device is configured to reduce a temperature of a target region such that the subcutaneous lipid-rich cells in the target region are reduced while non-lipid-rich cells proximate to the one or more heat exchanging surfaces are not significantly affected.

2. The cooling device of claim 1, wherein the cooling element is configured to reduce the temperature of the subcutaneous lipid-rich cells in the target region to between −20° C. and 5° C.

3. The cooling device of claim 2, wherein the cooling element is controlled according to a predetermined time-varying temperature profile.

4. The cooling device of claim 3, further comprising a processing unit programmed to cause the cooling element to operate to cool the subcutaneous lipid-rich cells in the target region to a sufficiently low temperature so as to selectively disrupt the subcutaneous lipid-rich cells.

5. The cooling device of claim 4, wherein the predetermined time-varying temperature profile comprises changing the temperature to be above about 30° C. and then lowering the temperature to about 0° C. or below.

6. A cooling device for removing heat from subcutaneous lipid-rich cells of a subject having skin, the cooling device comprising:
- a body;
- a surface configured to face the subject's skin;
- an inlet port configured to be coupled to a supply line;
- an outlet port configured to be coupled to an output line;
- a cooling element positioned along a flow path between the inlet and outlet ports such that liquid from the inlet port flows through the cooling element, wherein the cooling element is configured to reduce a temperature of the subcutaneous lipid-rich cells in the region to between −20° C. and 5° C. according to a predetermined time-varying temperature profile, the cooling element including:
  - a thermoelectric cooler,
  - an interface member,
  - an internal fluid chamber in thermal communication with the interface member,
  - a plurality of fluid ports in fluid communication with the internal fluid chamber, wherein the fluid ports are configured to allow liquid circulation through the internal fluid chamber, wherein the interface member is made of a metal or metal alloy and has at least one heat exchanging surface, and wherein the cooling element is coupled to the body such that the at least one heat exchanging surface forms at least a portion of the surface configured to face the subject's skin and the thermoelectric cooler is within the body,
- a processing unit programmed to
  - store predetermined time-varying cooling profiles for different target sites, at least one of the predetermined time-varying cooling profiles has at least three segments each including a predetermined period of time and associated setpoint temperature for a target site, and
  - control the cooling device according to the predetermined time-varying cooling profile to cause the cooling elements to operate to sequentially
    - cool the subcutaneous lipid-rich cells of the subject to reduce a temperature of the subcutaneous lipid-rich cells in the region to between −20° C. and 5° C. so as to selectively disrupt the subcutaneous lipid-rich cells, and
    - heat the subject's cooled tissue, and
- a sensing element proximate to the interface member; and
wherein the cooling device is configured to reduce the temperature of a target region such that lipid-rich cells in the target region are reduced while non-lipid-rich cells proximate to the heat exchanging surfaces are not significantly affected.

7. The device of claim 6, wherein the predetermined time-varying temperature profile comprises changing the temperature to above about 30° C. and then cooling to a temperature below 0° C.

8. The device of claim 6, wherein the supply line and/or the output line is a hose.

9. The device of claim 6, wherein the cooling element includes an additional thermoelectric cooler, wherein the internal fluid chamber is configured to circulate the liquid such that the liquid absorbs heat from each of the thermoelectric coolers.

\* \* \* \* \*